US007454973B2

(12) United States Patent
Baba et al.

(10) Patent No.: US 7,454,973 B2
(45) Date of Patent: Nov. 25, 2008

(54) ULTRASONIC INSPECTION METHOD AND ULTRASONIC INSPECTION EQUIPMENT

(75) Inventors: Atsushi Baba, Tokai-mura (JP); Naoyuki Kono, Mito (JP); Yoshinori Musha, Hitachiota (JP)

(73) Assignee: Hitachi, Ltd., Tokyo (JP)

( * ) Notice: Subject to any disclaimer, the term of this patent is extended or adjusted under 35 U.S.C. 154(b) by 391 days.

(21) Appl. No.: 11/393,832

(22) Filed: Mar. 31, 2006

(65) Prior Publication Data
US 2006/0219013 A1 Oct. 5, 2006

(30) Foreign Application Priority Data
Apr. 1, 2005 (JP) ............... 2005-106251

(51) Int. Cl.
*G01N 29/00* (2006.01)
*A61B 8/00* (2006.01)
(52) U.S. Cl. ............... 73/606; 73/602; 73/625; 73/628; 73/641; 600/443; 600/447
(58) Field of Classification Search ............ 73/606, 73/602, 624, 625, 628, 641; 600/441, 443, 600/447
See application file for complete search history.

(56) References Cited
U.S. PATENT DOCUMENTS

| 4,459,853 A * | 7/1984 | Miwa et al. ............ 73/626 |
| 4,537,073 A * | 8/1985 | Ooshiro et al. .......... 73/602 |
| 4,592,237 A * | 6/1986 | Ogura et al. ............ 73/602 |
| 4,817,614 A * | 4/1989 | Hassler et al. .......... 600/441 |
| 5,042,305 A * | 8/1991 | Takishita .............. 73/625 |
| 5,570,691 A * | 11/1996 | Wright et al. ........... 600/447 |
| 7,338,448 B2 * | 3/2008 | Hao et al. ............. 600/443 |
| 2006/0254359 A1* | 11/2006 | Langlois et al. ......... 73/606 |

FOREIGN PATENT DOCUMENTS

| JP | 60-91257 A | 5/1985 |
| JP | 3-122563 A | 5/1991 |
| JP | 09-292374 | 11/1997 |
| JP | 11-211708 A | 8/1999 |
| JP | 2001-153847 | 6/2001 |

OTHER PUBLICATIONS

Kondo, Rinsei, Ohashi, Yoshimasa, and Minomori Toshiro, "Digital Signal Processing in Measurements and Sensors", pp. 143-186, Digital Signal Processing Series vol. 12, published on May 20, 1993 by Syoukodo Publishing Inc.

* cited by examiner

*Primary Examiner*—Hezron Williams
*Assistant Examiner*—J M Saint Surin
(74) *Attorney, Agent, or Firm*—Crowell & Moring LLP

(57) ABSTRACT

In the ultrasonic inspection method and equipment, a high-resolution and high-S/N-ratio inspection image can be speedily acquired with ease-of-operability. Inspection of the inside of the inspection target is performed by changing incident angle of the ultrasonic wave oscillated from the array-probe ultrasonic sensor. Then, while performing the inspection, the array-probe ultrasonic sensor is sequentially displaced from the position to the position via the position by using the displacement member. This displacement allows acquisition of inspection images on each position basis. Finally, the inspection images thus acquired are visualized as a processed image by adding or averaging the inspection images by shifting the images by displacement quantity of the array-probe ultrasonic sensor.

10 Claims, 14 Drawing Sheets

ULTRASONIC INSPECTION METHOD AND ULTRASONIC INSPECTION EQUIPMENT

BACKGROUND OF THE INVENTION

1. Field of the Invention

The present invention relates to an ultrasonic inspection method, i.e., one type of nondestructive inspection techniques. More particularly, it relates to the ultrasonic inspection method and equipment therefor using an array-probe ultrasonic sensor.

2. Description of the Related Art

In the ultrasonic inspection methods intended for dealing with various types of structural materials as the inspection targets, from conventionally, detecting a defect is performed as follows: Namely, an ultrasonic sensor including a single element is used for transmission and reception of ultrasonic wave. Then, an ultrasonic signal reflected by a defect or the like inside an inspection target is detected. Finally, the defect is detected based on the propagation time and position of the ultrasonic sensor.

At this time, the ultrasonic sensor is caused to displace, then determining positions at which the reflected waves from the defect can be acquired. Moreover, size of the defect is identified by an integrating operation of differences in reception times of the reflected waves from the bottom surface (i.e., boundary surface at farther distance) of the inspection target or the surface (i.e., boundary surface at nearer distance) thereof, and material ultrasonic-wave velocity (i.e., ultrasonic-wave velocity inside material of the inspection target).

This method is often used for common-purpose defect inspections, because its operation principle is easy and straightforward, and because the equipment therefor is functional enough to be comparatively simple. In this method, however, the defect must be evaluated only from the reception times of the reflected ultrasonic waves after the reflected ultrasonic waves are measured. This complexity has required a skilled and proficient inspector for implementing the high-accuracy inspection, and also has necessitated a tremendous amount of time for completing the measurement.

Meanwhile, in recent years, as known as methods such as the phased array method and synthetic aperture method, the ultrasonic inspection methods have been developed which perform the inspection by allowing the inside of an inspection target to be imaged with high accuracy (Refer to, e.g., Non-Patent Document 1).

Here, first, the phased array method is a method based on the following principle: Namely, using the so-called array-probe ultrasonic sensor where a plurality of piezoelectric vibration elements are arranged, wavefronts of ultrasonic waves transmitted from the respective piezoelectric vibration elements interfere with each other. Then, the wavefronts will propagate in such a manner that the wavefronts have formed a superimposed wavefront as a result of the interference. Accordingly, by exercising a delay control over ultrasonic-waves transmission timings of the respective piezoelectric vibration elements to shift the respective timings with each other, it becomes possible to control incident angles of the ultrasonic waves and thereby to converge the ultrasonic waves.

Also, at the reception time of the ultrasonic waves as well, reflected ultrasonic waves received at the respective piezoelectric vibration elements are added n the manner where the reflected ultrasonic waves are sifted with each other. Similarly to the transmission time, this addition makes it possible to control reception incident angles of the ultrasonic waves, and to receive the ultrasonic waves in the manner where the focusing is achieved.

Moreover, as this phased array method, there has been generally known the linear scan scheme for scanning the piezoelectric vibration elements linearly, or the sectorial scan scheme for changing the transmission and reception directions of the ultrasonic waves in a sector-shaped configuration. In any case of the above-described schemes, it is possible to scan the ultrasonic waves at high speed without displacing the ultrasonic sensor, and to arbitrarily control incident angles of the ultrasonic waves and position of the focal depth without exchanging the ultrasonic sensor. Accordingly, these schemes can be said to be technologies which allow implementation of the high-speed and high-accuracy inspection.

On the other hand, the synthetic aperture method is a method based on the following principle: Namely, when a reflected ultrasonic signal is received after the ultrasonic wave is transmitted in such a manner that the ultrasonic wave will diffuse widely inside an inspection target, position of a defect, which turns out to become sound source of the reflected ultrasonic wave received, exists on an arc whose center is position of a piezoelectric vibration element which had transmitted the ultrasonic wave and has received the reflected ultrasonic wave, and whose radius is equal to propagation distance of the reflected ultrasonic wave. Here, while sequentially changing position of the piezoelectric vibration element, transmission and reception of the ultrasonic waves are performed. Then, computational operation for reception waveforms at the respective positions is performed on an electronic computer, thereby extending the reception waveforms in an arc-like configuration. On account of the above-described principle, this operation concentrates intersection points of the arcs on the existence position of the defect which becomes the reflection source of the ultrasonic waves. As a consequence, it becomes possible to identify the position of the defect.

From an actual and practical point-of-view, the synthetic aperture method is a technology for implementing the high-resolution imaging by using position of the ultrasonic sensor and an ultrasonic waveform signal at this position, and applying the computational-operation processing thereto on an electronic computer. Concerning contents of the computational-operation processing at this time, the description has been given in Non-Patent Document 1:

[Non-Patent Document 1] coauthors: Rinsei Kondo, Yoshimasa Ohashi, and Toshiro Minomori, "Digital Signal Processing in Measurements and Sensors", pp. 143-186, Digital Signal Processing Series Vol. 12, published on May 20, 1993 by Syoukodo Publishing Inc.

SUMMARY OF THE INVENTION

At first, of the above-described conventional technologies, in the case of the phased array method, the incident angle and convergence position of the ultrasonic wave are arbitrarily controlled using the plurality of piezoelectric vibration elements. This results in an advantage of being capable of performing the high-speed and high-accuracy inspection. In contrast thereto, however, the focusing is achieved only at a set focal-depth position. Accordingly, at a depth position at which the ultrasonic wave is not converged, the ultrasonic wave becomes non-converged. This, eventually, has resulted in a problem that the space resolution will be lowered at a depth position at which the focusing is not achieved.

Also, in this phased array method, the ultrasonic scans need to be performed in such a manner that the focusing is achieved at all the depth positions of an inspection target for each ultrasonic scan. At this time, however, there exists a limit to the transmission/reception repetition period of the ultrasonic wave. This has resulted in a problem that completing the measurement necessities a tremendous amount of time, which is not realistic.

Moreover, in this phased array method, the evaluation of a defect needs to be performed by watching an enormous number of inspection images which are divided in correspondence with the focal depths. This has resulted in a problem that evaluating these inspection images becomes an extremely complicated and troublesome task.

Next, of the above-described conventional technologies, in the case of the synthetic aperture method, the computational-operation processing is applied to the respective waveforms at the transmission and reception points of the ultrasonic wave on the electronic computer. This results in an advantage of being capable of implementing the high-resolution imaging. In contrast thereto, however, the ultrasonic wave needs to be transmitted in such a manner that, on principle, the ultrasonic wave will diffuse widely. Accordingly, as the propagation distance of the ultrasonic wave becomes longer, intensity (level) of the ultrasonic wave received becomes lower. On account of this, if attenuation of the ultrasonic wave due to the diffusion is large, and if the inspection target is thick and the propagation distance of the ultrasonic wave is long, the intensity of the ultrasonic wave at a point farther distant from the ultrasonic sensor becomes significantly weak. This has resulted in a problem that the reception of the reflected ultrasonic wave becomes difficult, and that the reflected ultrasonic wave becomes highly likely to undergo influences by various types of noises the typical of which is electric noise, and that the S/N ratio is lowered.

Furthermore, in this synthetic aperture method, the high-level computational-operation processing needs to be performed on the electronic computer. Accordingly, a time is necessitated for the computational operation. This, consequently, has resulted in a problem that the synthetic aperture method is not suitable as a method for evaluating the inspection images while performing the inspection on an actual site.

It is an object of the present invention to provide an ultrasonic inspection method and equipment therefor which allows a high-resolution and high-S/N-ratio inspection image to be speedily acquired with ease-of-operability.

The above-described object is accomplished by an ultrasonic inspection method including the steps of: Displacing transmission/reception position of ultrasonic wave relative to an inspection target by an array-probe ultrasonic sensor, performing inspection of the inspection target in accordance with sectorial scan scheme by using the array-probe ultrasonic sensor at the plurality of transmission/reception positions, and generating respective inspection result images at the plurality of transmission/reception positions into a single image.

Also, in addition to the above-described method, the above-described object is also accomplished by an ultrasonic inspection method including the steps of: Grasping quantity of the displacement of the transmission/reception position of the ultrasonic wave, and generating the single image by applying an addition or averaging processing to the respective inspection result images by shifting the images by the amount equivalent to the quantity of the displacement.

The above-described object is accomplished by ultrasonic inspection equipment including: An array-probe ultrasonic sensor, a scan unit for displacing transmission/reception position of ultrasonic wave by the array-probe ultrasonic sensor, a transmission/reception unit for transmitting/receiving a driving signal and a reception signal between the transmission/reception unit and the array-probe ultrasonic sensor, and allocating a delay time to the driving signal thereby to change convergence position and incident angle of the ultrasonic wave, a computer for applying an addition or averaging processing to ultrasonic-wave transmission/reception results at the plurality of ultrasonic-wave transmission/reception positions by shifting the results by the amount equivalent to quantity of the displacement, and a display unit for displaying a processing result in the computer as a single inspection image.

The above-described object is accomplished as follows: Changing incident angle of ultrasonic wave relative to an inspection target by using an array-probe ultrasonic sensor, displacing set-up position of the array-probe ultrasonic sensor in the inspection target, thereby to sequentially acquire inspection images on each set-up position basis, and visualizing the inspection images on each set-up position basis by adding or averaging the inspection images while sequentially shifting the images by the amount equivalent to quantity of the displacement of the array-probe ultrasonic sensor.

Here, the above-described object is also accomplished as follows: In the addition or averaging of the inspection images, inclination angle of each inspection image will be corrected in response to inclination of surface of the inspection target which appears in the displacement of the set-up position of the array-probe ultrasonic sensor in the inspection target.

Also, the above-described object is accomplished as follows: Changing incident angle of ultrasonic wave relative to an inspection target by using part of piezoelectric vibration elements inside an array-probe ultrasonic sensor, displacing ultrasonic-wave transmission/reception position of the array-probe ultrasonic sensor in the inspection target by sequentially switching the part of the piezoelectric vibration elements inside the array-probe ultrasonic sensor, thereby to sequentially acquire inspection images on each ultrasonic-wave transmission/reception position basis, and visualizing the inspection images on each ultrasonic-wave transmission/reception position basis by adding or averaging the inspection images while sequentially shifting the images by the amount equivalent to quantity of the displacement of the part of the piezoelectric vibration elements inside the array-probe ultrasonic sensor.

Next, the above-described object is also accomplished by including: An array-probe ultrasonic sensor including a plurality of piezoelectric vibration elements, a pulser for supplying a transmission signal to each piezoelectric vibration element of the array-probe ultrasonic sensor, a receiver for inputting a reception signal from each piezoelectric vibration element of the array-probe ultrasonic sensor, a delay control unit for setting a delay time to the transmission signal and the reception signal, the delay time being different on each piezoelectric-vibration-element basis, a data storage unit for storing ultrasonic waveforms received at the array-probe ultrasonic sensor, a sensor displacement unit for scanning the array-probe ultrasonic sensor with respect to an inspection target, a scan control unit for controlling the scan, a displacement-quantity detection unit for measuring displacement quantity of the array-probe ultrasonic sensor, an image-processing computer for generating a plurality of inspection images from the ultrasonic waveforms stored in the data storage unit, and adding the plurality of inspection images by shifting the images by the amount of the displacement quantity measured in the displacement-quantity detection unit of the array-probe ultrasonic sensor, and a display unit for displaying the inspection images and an inspection image acquired from the addition.

Here, the above-described computer may also be a one which, in adding or averaging the plurality of inspection images, will correct inclination angle of each inspection image in response to inclination of surface of the inspection target which appears in the displacement of the set-up position of the array-probe ultrasonic sensor in the inspection target.

Similarly, the above-described object is also accomplished by including: An array-probe ultrasonic sensor including a plurality of piezoelectric vibration elements whose number is larger than a number needed for operation as the array-probe ultrasonic sensor, a pulser for supplying a transmission signal to each piezoelectric vibration element of the array-probe ultrasonic sensor, a transmission switching circuit for switching a piezoelectric vibration element to which, of the respective piezoelectric vibration elements of the array-probe ultrasonic sensor, the output from the pulser will be supplied, a receiver for inputting a reception signal from each piezoelectric vibration element of the array-probe ultrasonic sensor, a reception switching circuit for switching a piezoelectric vibration element which, of the respective piezoelectric vibration elements of the array-probe ultrasonic sensor, will supply the reception signal to the receiver, a delay control unit for setting a delay time to the transmission signal and the reception signal, the delay time being different on each piezoelectric-vibration-element basis, a data storage unit for storing ultrasonic waveforms received at the array-probe ultrasonic sensor, a sensor displacement unit for scanning the array-probe ultrasonic sensor with respect to an inspection target, a scan control unit for controlling the scan, a displacement-quantity detection unit for measuring displacement quantity of the array-probe ultrasonic sensor, an image-processing computer for generating a plurality of inspection images from the ultrasonic waveforms stored in the data storage unit, and adding or averaging the plurality of inspection images by shifting the images by the amount of the displacement quantity measured in the displacement-quantity detection unit of the array-probe ultrasonic sensor, and a display unit for displaying the inspection images and an inspection image acquired from the addition.

According to the present invention, the inspection of the inside of an inspection target is performed in a manner of changing the incident angles of the ultrasonic waves oscillated from the array-probe ultrasonic sensor. Also, the set-up position of the array-probe ultrasonic sensor is sequentially displaced. Moreover, the inspection images acquired at the respective inspection positions are visualized by adding or averaging the inspection images while shifting the images by the displacement quantity of the array-probe ultrasonic sensor. This allows acquisition of the convergence effect on the ultrasonic waves without setting the focal depths in particular detail. Accordingly, it becomes possible to acquire the high-resolution inspection images at almost all the depth positions. This permits implementation of the high-accuracy nondestructive inspection. Furthermore, the addition or averaging of the inspection images makes it possible to reduce the random noises, thereby allowing an enhancement in the S/N ratio of the resultant inspection image.

Also, according to the present invention, there are provided the array-probe ultrasonic sensor including the plurality of piezoelectric vibration elements, the pulser for transmitting the transmission signal with each piezoelectric vibration element of the array-probe ultrasonic sensor, and the receiver for transmitting/receiving the reception signal therewith, the delay control unit for exercising the time control by setting the delay time to the transmission signal and the reception signal, the delay time being made variable on each piezoelectric-vibration-element basis, the data storage unit for storing the ultrasonic waveforms transmitted and received at the array-probe ultrasonic sensor, the sensor displacement unit for scanning the array-probe ultrasonic sensor, the scan control unit for controlling the scan, the displacement-quantity detection unit for measuring the displacement quantity of the array-probe ultrasonic sensor, the image-processing unit for generating the plurality of inspection images from the ultrasonic waveforms stored, and adding or averaging the plurality of inspection images by shifting the images by the amount of the displacement quantity measured in the displacement-quantity detection unit of the array-probe ultrasonic sensor, and the display unit for displaying the inspection images and the inspection image acquired from the addition. This makes it possible to acquire the convergence effect on the ultrasonic waves without setting the focal depths in particular detail. Accordingly, it has become possible to implement the high-resolution inspection images, thereby allowing implementation of the high-accuracy nondestructive inspection.

Also, as a result, according to the present invention, there is provided the processing-contents switch unit for switching between the inspection methods such as the linear scan scheme and the sectorial scan scheme, i.e., the conventional inspection methods using the array-probe ultrasonic sensor, and the above-described inspection image processing method. This allows implementation of the operations as well which are basically the same as those in the conventional inspection methods.

Similarly, according to the present invention, in the inspection using the array-probe ultrasonic sensor, it becomes possible to acquire the convergence effect on the ultrasonic waves without setting the focal depths in particular detail. As a result, it becomes possible to acquire the high-resolution inspection images at almost all the depth positions even if the positions are distant from the sensor.

Furthermore, according to the present invention, it becomes possible to acquire the high-resolution and high-S/N-ratio inspection images even if, unlike the synthetic aperture method, the high-level computational operation is not performed with a long time spent. This allows the inspection results to be speedily evaluated even on an actual site of the inspection.

According to the present invention, it becomes possible to acquire the convergence effect on the ultrasonic waves without setting the focal depths in particular detail. This allows the high-resolution and high-S/N-ratio inspection image to be speedily acquired with ease-of-operability. As a result, it becomes possible to carry out the high-accuracy and excellent-reliability nondestructive inspection.

Other objects, features and advantages of the invention will become apparent from the following description of the embodiments of the invention taken in conjunction with the accompanying drawings.

DETAILED DESCRIPTION OF THE INVENTION

Figure 1:
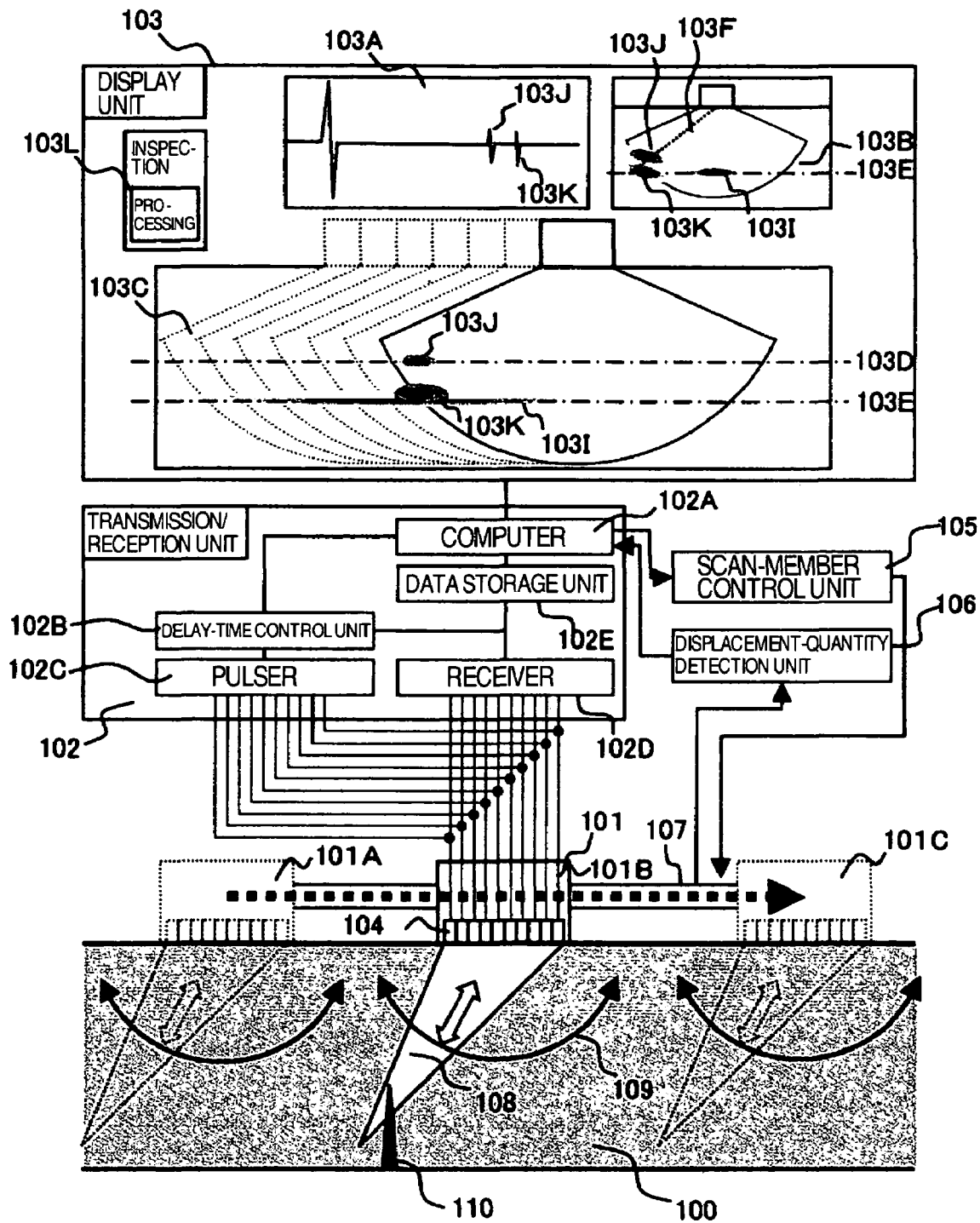
FIG. 1 is a configuration diagram for illustrating a first embodiment of the ultrasonic inspection method and the ultrasonic inspection equipment according to the present invention.

Hereinafter, referring to the drawings, the detailed explanation will be given below concerning embodiments of the ultrasonic inspection method and equipment according to the present invention.

FIG. 1 illustrates a first embodiment of the present invention. As illustrated therein, the first embodiment includes an inspection target 100, an array-probe ultrasonic sensor 101 for causing ultrasonic wave to enter this inspection target, a transmission/reception unit 102, a display unit 103 for displaying reception signals and inspection images, a scan-member control unit 105 for scanning the array-probe ultrasonic sensor 101, a displacement-quantity detection unit 106 for detecting displacement quantity of the array-probe ultrasonic sensor 101, and a sensor displacement (or scan) member 107 for scanning the array-probe ultrasonic sensor 101.

Here, at first, the array-probe ultrasonic sensor 101, as illustrated therein, essentially includes a plurality of piezoelectric vibration elements 104 for generating and receiving ultrasonic waves. After being set up on inspection surface of the inspection target 100, the array-probe ultrasonic sensor 101 generates the ultrasonic wave 108 in accordance with driving signals supplied from the transmission/reception unit 102. Then, the sensor 101 causes the ultrasonic wave 108 to propagate inside the inspection target 100. Next, the sensor 101 detects the reflected ultrasonic wave which occurs from the propagation, then inputting the reception signals into the transmission/reception unit 102.

Moreover, the transmission/reception unit 102 performs the transmission and reception of the ultrasonic wave by the array-probe ultrasonic sensor 101. For this purpose, the transmission/reception unit 102 includes a computer 102A, a delay-time control unit 102B, a pulser 102C, a receiver 102D, and a data storage unit 102E. The pulser 102C supplies the driving signals to the array-probe ultrasonic sensor 101. Then, the receiver 102D processes the reception signals inputted from the array-probe ultrasonic sensor 101 in response to this supply.

At this time, the computer 102A controls the delay-time control unit 102B, the pulser 102C, the receiver 102D, and the data storage unit 102 so that necessary operations will be able to be acquired. First, the delay-time control unit 102B controls both timing for the driving signals outputted from the pulser 102C and input timing for the reception signals by the receiver 102D. The unit 102B exercises this control so that operation of the array-probe ultrasonic sensor 101 based on the phased array scheme will be able to be acquired.

What is referred to as "operation of the array-probe ultrasonic sensor 101 based on the phased array scheme" means the operation of transmitting and receiving the ultrasonic wave 108 in a manner where focal depth and incident angle 109 of the ultrasonic wave 108 are controlled. This operation turns out to supply the reception signals from the receiver 102D to the data storage unit 102E.

Then, the data storage unit 102E processes the reception signals supplied thereto, then causing the computer 102A to store the processed reception signals as storage data. Based on this data, the computer 102A executes the following operation: The computer 102A applies a superimposition processing to the ultrasonic waveforms in response to delay times. Here, the waveforms are acquired in the respective piezoelectric vibration elements. In this way, the computer 102A applies the image processing to the waveforms of the respective ultrasonic waves on each incident-angle basis. Moreover, the computer 102A supplies the image-processed waveforms to the display unit 103, then causing the unit 103 to display the image-processed waveforms as a plurality of inspection images 103B.

At this time, furthermore, in correspondence with the operations of the scan-member control unit 105 and the displacement-quantity detection unit 106, the computer 102A applies an addition or averaging processing to the plurality of inspection images 103B acquired at the respective positions. Moreover, the computer 102A causes the display unit 103 to display the resultant processed inspection image as a processed image 103C.

Also, the display unit 103 displays the inspection images as described above, and also includes a function of displaying a superimposed waveform 103A corresponding to position of an arbitrary ultrasonic-wave incident angle 103F of the inspection images. Incidentally, the detailed explanation will be given later regarding the processing contents by the computer 102A and the operation of the display unit 103.

By the way, in FIG. 1, the drawing has been given assuming the case where a defect 110 exists on the bottom side of the inspection target 100. When, in this way, the defect 110 exists on the bottom side of the inspection target 100, echoes are as follows which will be observed in the inspection images 103B and the processed image 103C on the display unit 103: An echo due to the bottom of the defect on the bottom position 103E, i.e., the so-called defect corner echo 103K, an echo due to the tip of the defect, i.e., the so-called defect tip echo 103J, and an echo due to the bottom of the inspection target 100, i.e., the so-called bottom echo 103I. Simultaneously, in the superimposed waveform 103A as well, reflected waves corresponding to these echoes are observed as the defect corner echo 103K and the defect tip echo 103J.

Then, in this state, when performing depth-sizing evaluation of the defect on the bottom side, the bottom position 103E and defect tip echo position 103D of the echoes acquired within the processed image 103C will be used. On account of this, a position control unit included in the scan-member control unit 105 receives, from the computer 102A, a displacement signal including displacement speed and the displacement quantity. Moreover, based on this displacement signal, the position control unit drives the sensor displacement member 107, thereby displacing the array-probe ultrasonic sensor 101 to change the set-up position of the array-probe ultrasonic sensor 101 as shown by positions 101A, 101B, and 101C.

At this time, the sensor displacement member 107, although not illustrated, includes a sensor-position detection member. The detection signal therefrom is supplied to the displacement-quantity detection unit 106. This detection signal allows the displacement-quantity detection unit 106 to measure an actual displacement quantity of the array-probe ultrasonic sensor 101. Incidentally, in FIG. 1, the case is shown where the array-probe ultrasonic sensor 101 is displaced from the position 101A at the inspection start time to the position 101C at the inspection termination time via the position 101B halfway therebetween.

The displacement quantity measured in this way is transmitted from the displacement-quantity detection unit 106 to the computer 102A, then being used for processing the inspection images. This processing will be explained in detail later but, if it is explained briefly, the measured displacement quantity is used as follows: The displacement quantity is measured at each inspection position of the array-probe ultrasonic sensor 101. Then, the measured displacement quantity is used for carrying out the addition or averaging of the inspection images by shifting pixel positions of the inspection images by the amount equivalent to this displacement quantity within the computer 102A.

By the way, the ultrasonic inspection equipment according to this embodiment allows not only implementation of the operation by the above-described addition or averaging processing of the inspection images, but also implementation of the operations such as the linear scan and the sectorial scan by the conventional inspection equipment using the array-probe ultrasonic sensor. Consequently, in this embodiment, in order to switch between the above-described addition or averaging processing mode of the inspection images and these conventional operation modes, a switch-operated or button-operated processing-contents switch unit 103L is provided within the display unit 103. This switch unit allows the switching of the processing contents based on software of the computer 102A.

Next, referring to FIG. 2, the explanation will be given below regarding the operation of the array-probe ultrasonic sensor 101 in this embodiment. As described above, this array-probe ultrasonic sensor 101 includes the arrangement of the plurality of piezoelectric vibration elements 104. These piezoelectric vibration elements 104 are driven by the electric signals supplied from the transmission/reception unit 102, thus being vibrated by the piezoelectric effect to emit the ultrasonic wave 108. At this time, the delay-time control unit 102B allocates mutually independent time delays to the electric signals 201 supplied to the respective piezoelectric vibration elements 104 at this time.

Then, wavefronts 202 of the ultrasonic waves emitted from the respective piezoelectric vibration elements 104 interfere with each other. This interference forms a superimposed wavefront 203. As a result, it becomes possible to converge the ultrasonic wave 108 at an arbitrary depth position 204, and to control incident angle 205 of the ultrasonic wave 108. By the way, concerning a method for setting this depth position, in this embodiment, the focal point is set at the bottom of the inspection target 100 or at a position deeper than that. This setting is performed in order to take plate thickness of the inspection target 100 into consideration. This setting makes it possible to suppress the diffusion and attenuation of the ultrasonic wave, which becomes the problem when the synthetic aperture method is applied to the inspection. Implementation of this suppression allows the inspection to be carried out with high S/N ratio even if the propagation distance of the ultrasonic wave is considerably long.

Also, at this time, in order to acquire the inspection images 103B, the incident angle 205 of the ultrasonic wave 108 will be changed with a predetermined pitch and over a range 109 to be used for the inspection. The pitch of the incident angle 205 of the ultrasonic wave at this time can be arbitrarily set when carrying out the inspection. This angle pitch, however, depends on the time resolution set by the delay-time control unit 102B. The time resolution represents a minimum time pitch which can be set. Accordingly, the inspection will be performed with the angle pitch which is made larger than a minimum time resolution settable by the delay-time control unit 102B.

Next, referring to FIG. 3, the explanation will be given below concerning a concrete method for controlling the delay times at this time. At first, here, the following delay-time pattern 300 is shown as an example: Namely, the focal point is formed at a constant distance with the directly-under point of center of the array-probe ultrasonic sensor 101 selected as the criterion. Then, the incident angle of the ultrasonic wave to be used for the inspection is set at values which range from 10° to 170° with a 10-°pitch. The element number at this time is defined as follows: In the array-probe ultrasonic sensor 101, the element positioned at one end of the piezoelectric vibration elements 104, i.e., the element positioned at the left end in FIG. 1 and FIG. 2 here, is defined as No. 1. Accordingly, when the number of the piezoelectric vibration elements 104 is M, the element number of the element positioned at the right end turns out to become No. M.

Figure 2:
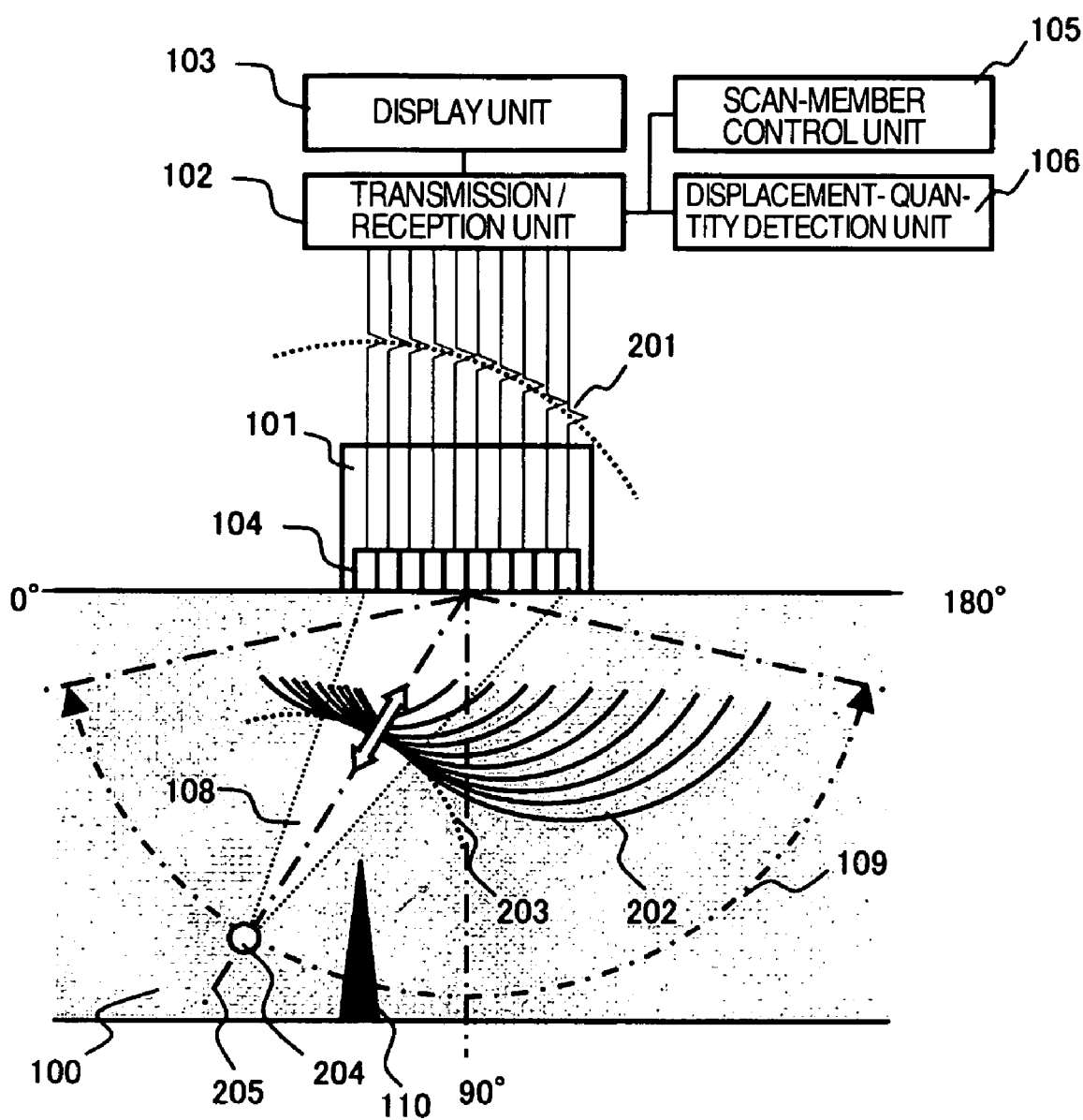
FIG. 2 is a schematic diagram for explaining operation of an embodiment of the ultrasonic inspection method and the ultrasonic inspection equipment according to the present invention.
Figure 3:
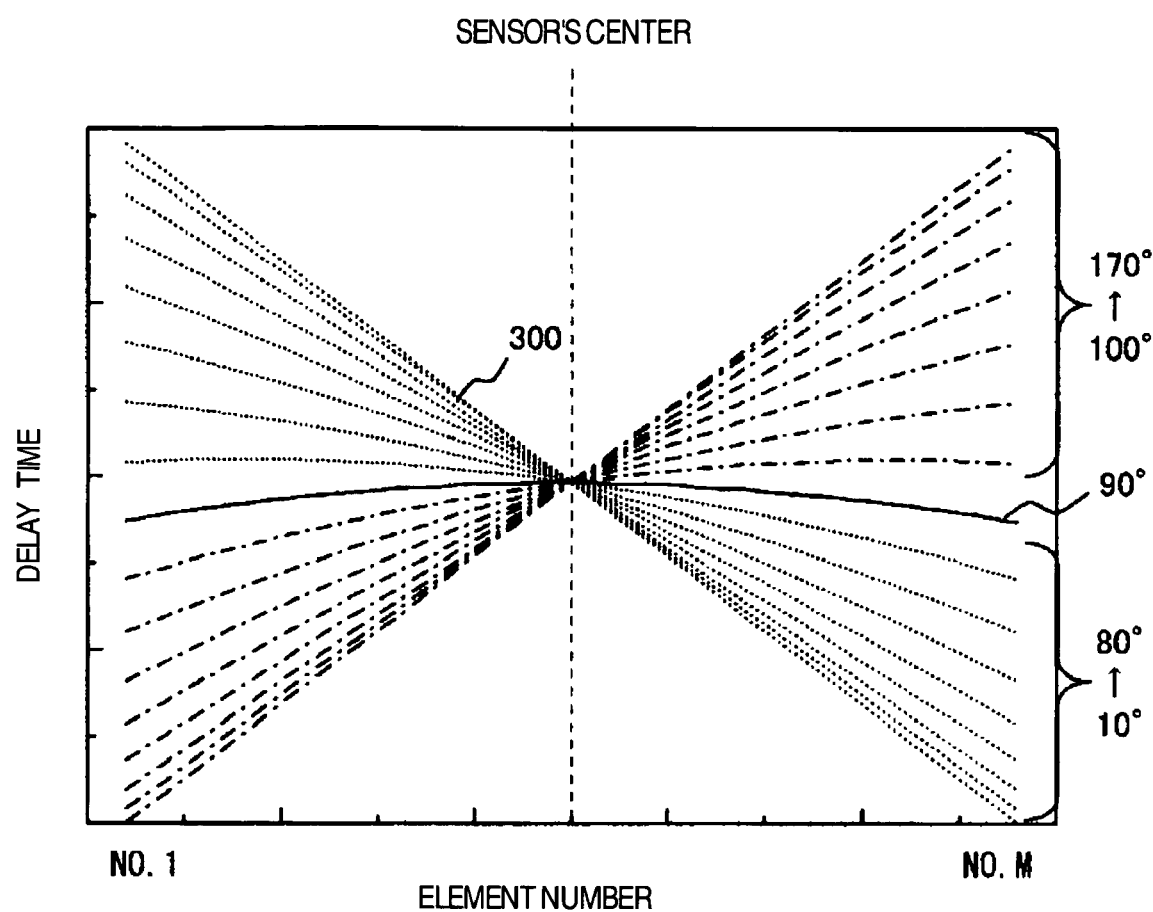
FIG. 3 is an explanatory diagram for illustrating an example of delay time pattern allocated to piezoelectric vibration elements of an array-probe ultrasonic sensor in the first embodiment of the present invention.

Moreover, the range of angle of 10° to angle of 80° shown by dashed lines is a delay-time pattern where the focal point is formed in the range of angle of 10° to angle of 80° at lower-left in FIG. 2. The solid line denotes the directly-under point of the center of the array-probe ultrasonic sensor 101. The range of angle of 100° to angle of 170° shown by alternate dashed lines is a delay-time pattern where the focal point is formed in the range of angle of 100° to angle of 170° at right-left in FIG. 2. In this way, by converging the ultrasonic wave 108 at the arbitrary position, it becomes possible to prevent the diffusion and attenuation of the ultrasonic wave which is the weak point of the synthetic aperture method.

Furthermore, the delay-time pattern 300 like this is calculated using the computer 102A. Then, the delay-time pattern calculated is transmitted to the delay-time control unit 102B, thereby performing the control so that the transmission and reception of the ultrasonic wave 108 can be performed. In this way, the scan method where the incident angle is continuously changed while keeping the ultrasonic-wave convergence distance constant is referred to as the sectorial scan method.

Figure 4:
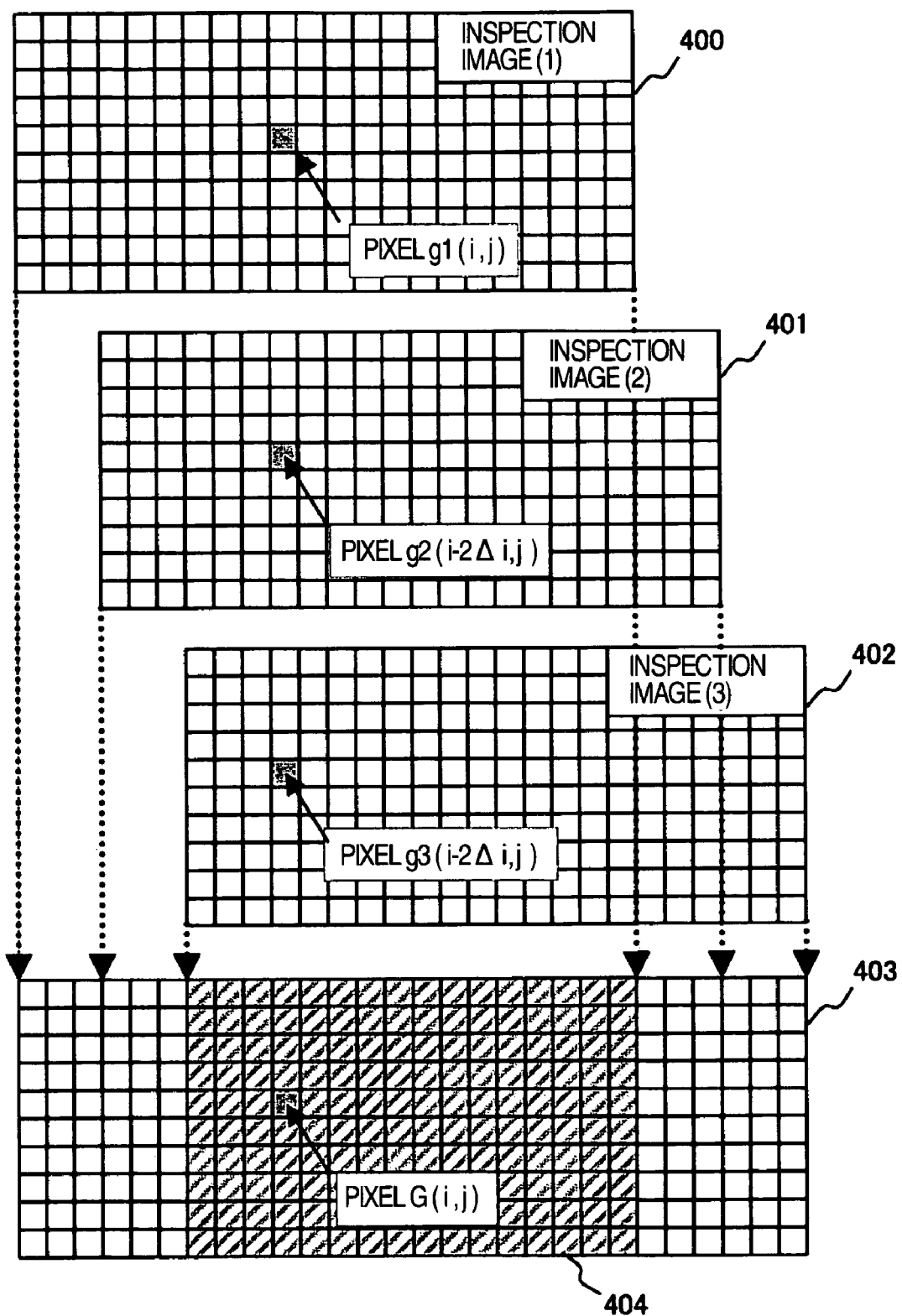
FIG. 4 is a schematic diagram for explaining an addition or averaging processing of inspection images in the first embodiment of the present invention.

Next, referring to FIG. 4 and FIG. 5, the detailed explanation will be given below concerning the processing of the inspection images executed by the computer 102A. Here, at first, FIG. 4 schematically illustrates contents of the processing of the inspection images within the computer 102A. Now, it is assumed that the array-probe ultrasonic sensor 101 is horizontally displaced by a displacement quantity X[m] from the position of an inspection image 400 acquired at the inspection start position 101A. Unchanging the storage region of the inspection image at this time results in a position shift of the image. Accordingly, correcting the position shift will be performed using the measurement value by the displacement-quantity detection unit 106.

Now, it is assumed that, when the sensor displacement quantity is X[m], a position shift equivalent to Δ [pixel] occurs in the inspection image in the display unit 103. In this case, as shown by the following (Expression 1), the addition is performed by shifting the amount equivalent to Δ [pixel]. Here, G (i,j) is value of a pixel at pixel address (i,j) of a processed image 403, and $g_n$ (i,j) is value of a pixel at the pixel address (i,j) of the n-th inspection image.

[Expression 1]

$$G(i, j) = \sum_{i}^{n} g_n(i - (n-1)\Delta, j)$$ Expression 1 where, $g_n(i, j) = 0$ if $i < (n-1)\Delta$

At this time, in FIG. 4, as an example for showing the contents of the processing, the case is schematically illustrated where the processed image 403 is acquired by adding the three pieces of inspection images 400, 401, and 402. When performing the evaluation of a defect, as shown by attaching the hatching within the processed image 403, the evaluation is performed in an area 404 where the inspection images in the same number within the processed image are processed. The reason for this is that, when the addition or averaging processing is performed, signal intensity of the pixels differ between an area 403 where the processing number is equal and an area where the processing number is different.

Figure 5:
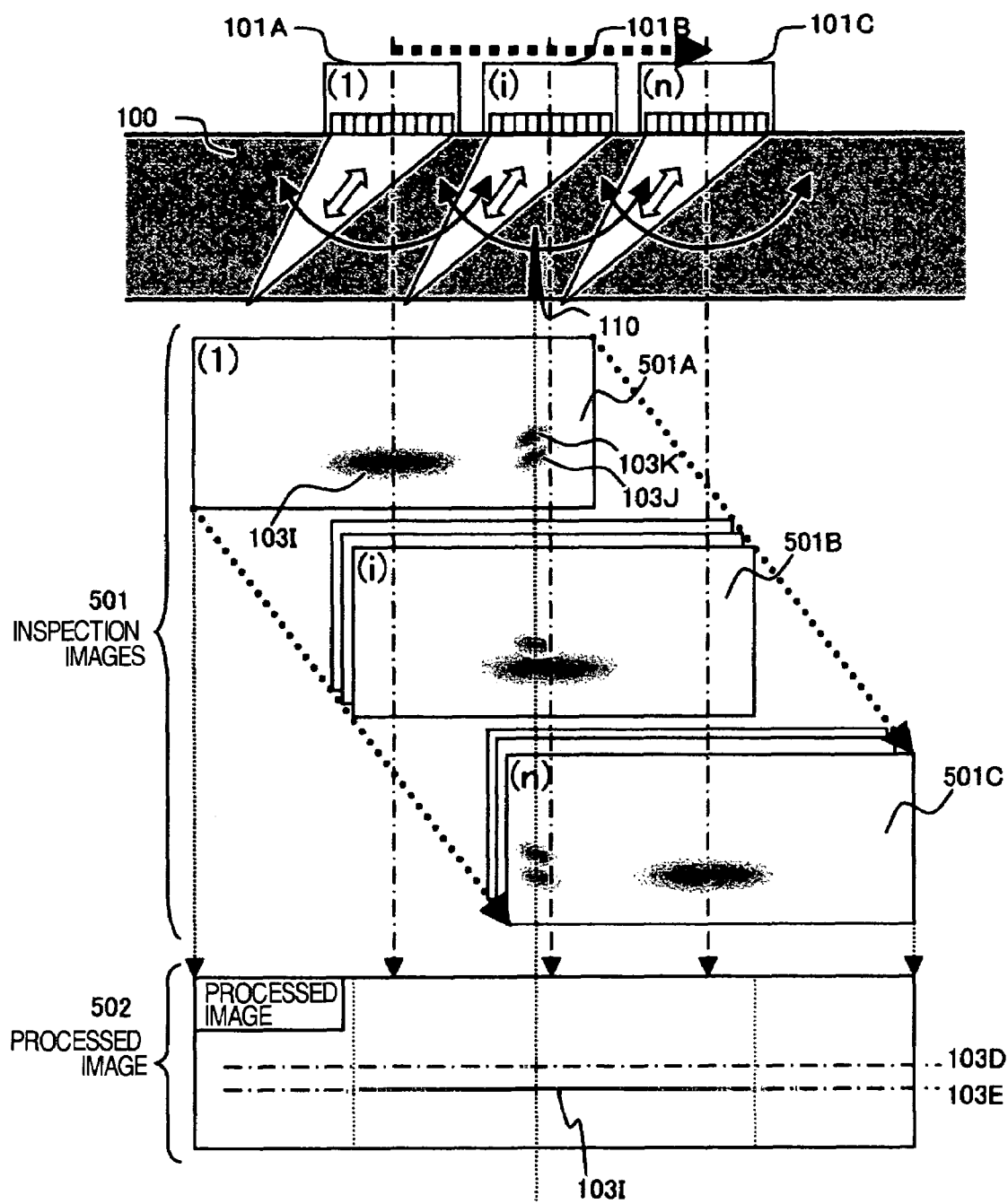
FIG. 5 is an explanatory diagram for illustrating an example of the addition or averaging processing of inspection images in the first embodiment of the present invention.

Meanwhile, FIG. 5 illustrates the contents explained in FIG. 4 in accompaniment with the actual inspection situation. In inspection images 501 in this drawing, a (1)-st inspection image 501A corresponds to the inspection image at the inspection start position 101A. Hereinafter, an (i)-th inspection image corresponds to the inspection image 101B, and an (n)-th inspection image corresponds to the inspection image 101C. Consequently, this drawing indicates that the n pieces of inspection images 501 inspected at the respective positions have been acquired.

Incidentally, this example illustrates the case where the surface of the inspection target 100 on which the array-probe ultrasonic sensor 101 is set up is parallel to the bottom, i.e., the inspection target 100 is part of the plate material and tube material. Accordingly, in these inspection images, the bottom echo 103I from the bottom is acquired directly under the set-up position of the array-probe ultrasonic sensor 101. Also, if the defect enters from the bottom side, the defect corner echo 103K and the defect tip echo 103J turns out to be observed.

Then, as illustrated in FIG. 4, a processed image 502 is acquired by applying the addition or averaging processing to the inspection images 501 including these images by shifting the inspection images by the pixel number equivalent to the quantity of the displacement of the array-probe ultrasonic sensor 101. Moreover, the characteristic of this processed image 502 is that, as shown by sandwiching the portion with two broken lines, the bottom echo 103I with substantially the same order of intensity is acquired in the portion to which the addition or averaging processings are applied at the same number.

Furthermore, at this time, with respect to the defect corner echo 103K and the defect tip echo 103J, only the signal at a real defect position selectively remains by the superimposition of the ultrasonic waves entering from the various angles. These images are displayed on the display unit 103, then being used for confirming the defect position and evaluating the defect depth. The further detailed explanation will be given later concerning this subject.

Figure 6:
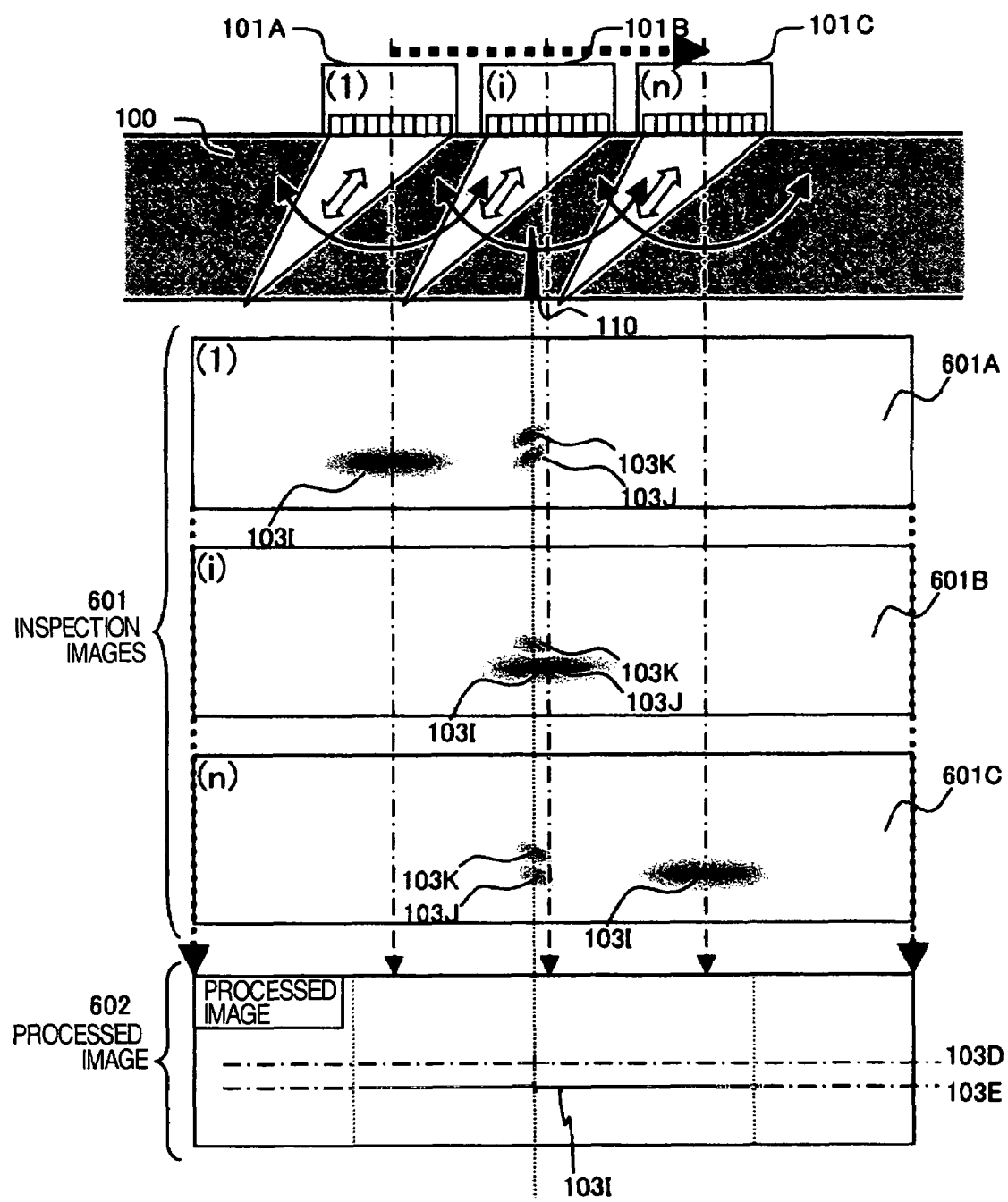
FIG. 6 is an explanatory diagram for illustrating another example of the addition or averaging processing of the inspection images in the first embodiment of the present invention.

Next, FIG. 6 illustrates the processing according to a second embodiment of the present invention. This processing is about the case where the range of the inspection images which become the inspection area is set over the entire scan area by the array-probe ultrasonic sensor 101, and the case where the inspection-image size is also inspected in the determined state. Namely, using the displacement quantity of the array-probe ultrasonic sensor 101 detected by the displacement-quantity detection unit 106, the inspection image is acquired by shifting, by the pixel number equivalent to the displacement quantity of the array-probe ultrasonic sensor 101, and superimposing the inspection images acquired at the respective inspection positions within the range of the inspection images set in advance.

Accordingly, in this second embodiment, at all the positions from the inspection start position (1) to the inspection termination position (n), the inspection images have become the same area. As a result, there exists no necessity for shifting the inspection images in accordance with the displacement quantity of the array-probe ultrasonic sensor 101. This makes it possible to acquire the processed image 502 by merely adding or averaging inspection images 601A, 601B, and 601C. Consequently, the processing contents in this case can be represented by the following (Expression 2). Here, this (Expression 2) indicates the case of the addition.

[Expression 2]

$$G(i, j) = \sum_{i}^{n} g_n(i, j)$$ Expression 2

The characteristic of this processed image becomes basically the same as the case in the first embodiment. Namely, with respect to the defect corner echo 103K and the defect tip echo 103J, only the signal at a real defect position selectively remains by the superimposition of the ultrasonic waves entering from the various angles.

Figure 7:
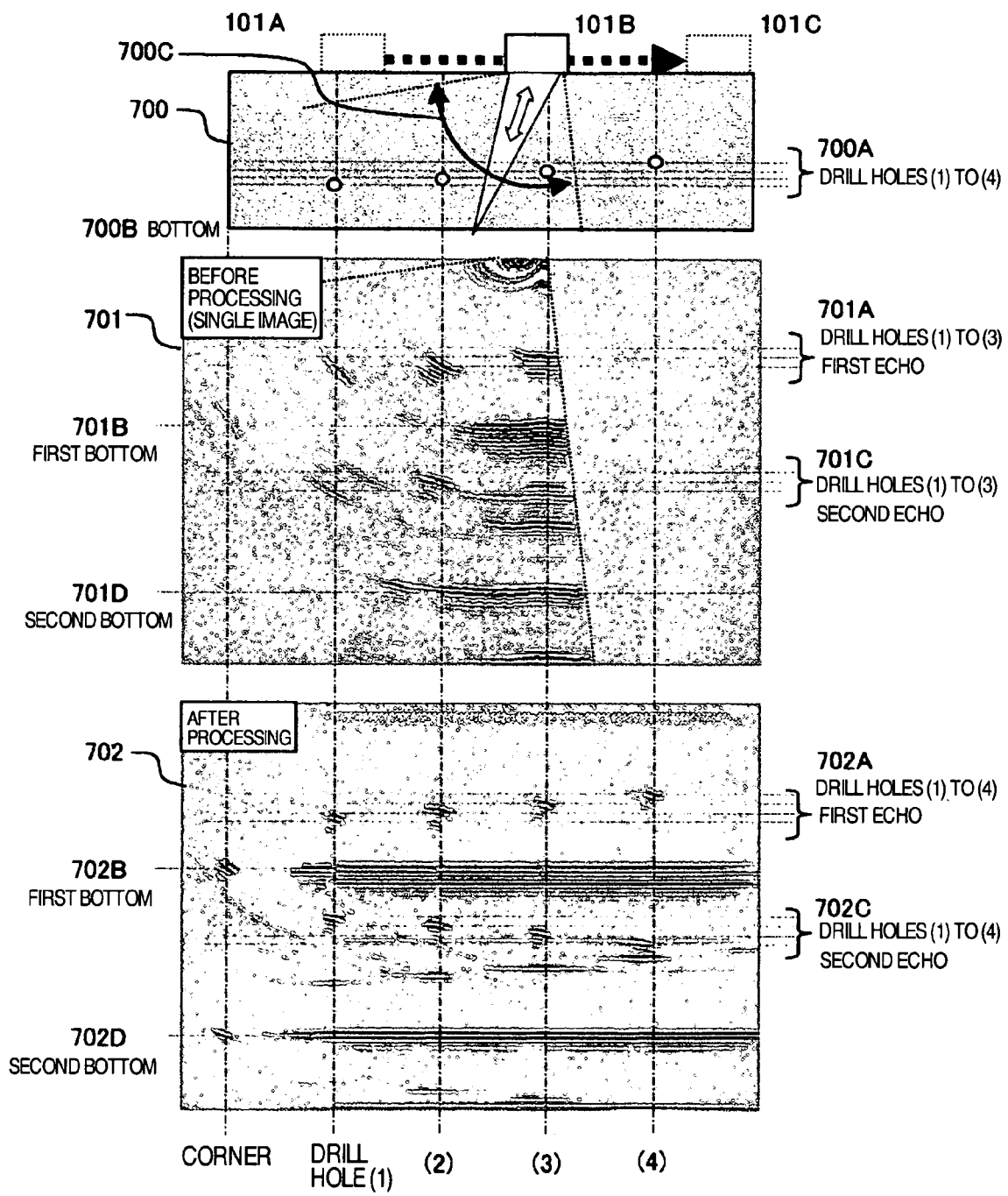
FIG. 7 is an explanatory diagram for illustrating an example of inspection image display acquired by the first embodiment of the present invention.

Next, referring to FIG. 7, the explanation will be given below regarding an application example of the present methodology. At first, in FIG. 7, a test body 700, i.e., an object which becomes the test body, is used as the inspection target. In this test body 700, a plurality of holes referred to as "drill holes" here are artificially provided at different-depth (i.e., thickness direction) positions in a steel plate material by using a hole-boring tool. These drill holes are bored so as to be regarded and utilized as defects. FIG. 7 illustrates a plurality of inspection images, and a processed image acquired by adding the plurality of inspection images. As the drill holes 700A at this time, the four holes (1), (2), (3), and (4) are provided.

Moreover, here, the sectorial scan is performed by setting the incident angle 700C of the ultrasonic wave by the array-probe ultrasonic sensor 101 at the range from angle of 10° to angle of 100°. Consequently, in a single inspection image 701 by the sensor position 101B, an echo due to the drill hole (4) is not observed, but echoes 701A corresponding to the drill holes (1) to (3) and a bottom echo 701B are observed.

Also, here, the focal point of the ultrasonic wave by the array-probe ultrasonic sensor 101 is set at the position somewhat deeper than the bottom 700B. On account of this, in the single inspection image 701, a drill-hole echo 701C due to the ultrasonic wave reflected at the bottom is observed as a second echo. Furthermore, a bottom echo 701D due to the ultrasonic wave which reciprocates two times inside the test body 700 is observed as a second bottom echo. Accordingly, in this embodiment, the effect resulting from converging the ultrasonic wave is obtained.

In addition, this single inspection image 701 also indicates that all the echoes present an arc-shaped configuration with the incoming position 101B of the ultrasonic wave as the center. Furthermore, this single inspection image 701 also indicates that any of the drill-hole echoes 701A is more expanded than sizes of the actual drill holes, and that the bottom echo 701B is observed only in the area directly under the sensor.

Next, a processed image 702 is obtained by acquiring and adding the single inspection image like this while displacing the array-probe ultrasonic sensor 101 from the inspection start position 101A to the inspection termination position 11C. In the respective inspection images from the inspection start position 101A to the inspection termination position 11C, this processed image 702 is visualized by the ultrasonic waves entering from the various angles seen from the respective drill holes (1), (2), (3), and (4).

As a result, the following principle which is more or less similar to the synthetic aperture method turns out to exert its influences. Namely, the drill-hole echoes remain even when superimposed, since the drill-hole echoes exist in the large number of single inspection images. Meanwhile, the echoes due to the other portions are thinned by the superimposition of the plurality of images, since such echoes appear in only a specific single inspection image. Accordingly, as illustrated in an after-processing image 702, it turns out that the echoes over the entire inspection images are acquired with an excellent S/N ratio.

Also, at this time, as described above, the focal point of the array-probe ultrasonic sensor 101 is set at the position deeper than the bottom 700B. Accordingly, with respect to the drill-hole echo 701C due to the bottom reflection as well, the focusing can be achieved. As a consequence, in the after-processing image 702 as well, the inspection images can be acquired where the second echo is observed. Similarly, it turns out that intensity of a first drill-hole echo 702A and that of a second drill-hole echo 702C are of substantially the same order. This fact indicates that, as a result of converging the ultrasonic wave at the position deeper than the bottom 700B, there exists none of the intensity lowering due to the diffusion and attenuation of the ultrasonic wave even at the position deeper than the bottom. Consequently, it turns out that the effect of the defect inspection method according to the present invention has been demonstrated in this point as well.

Figure 8:
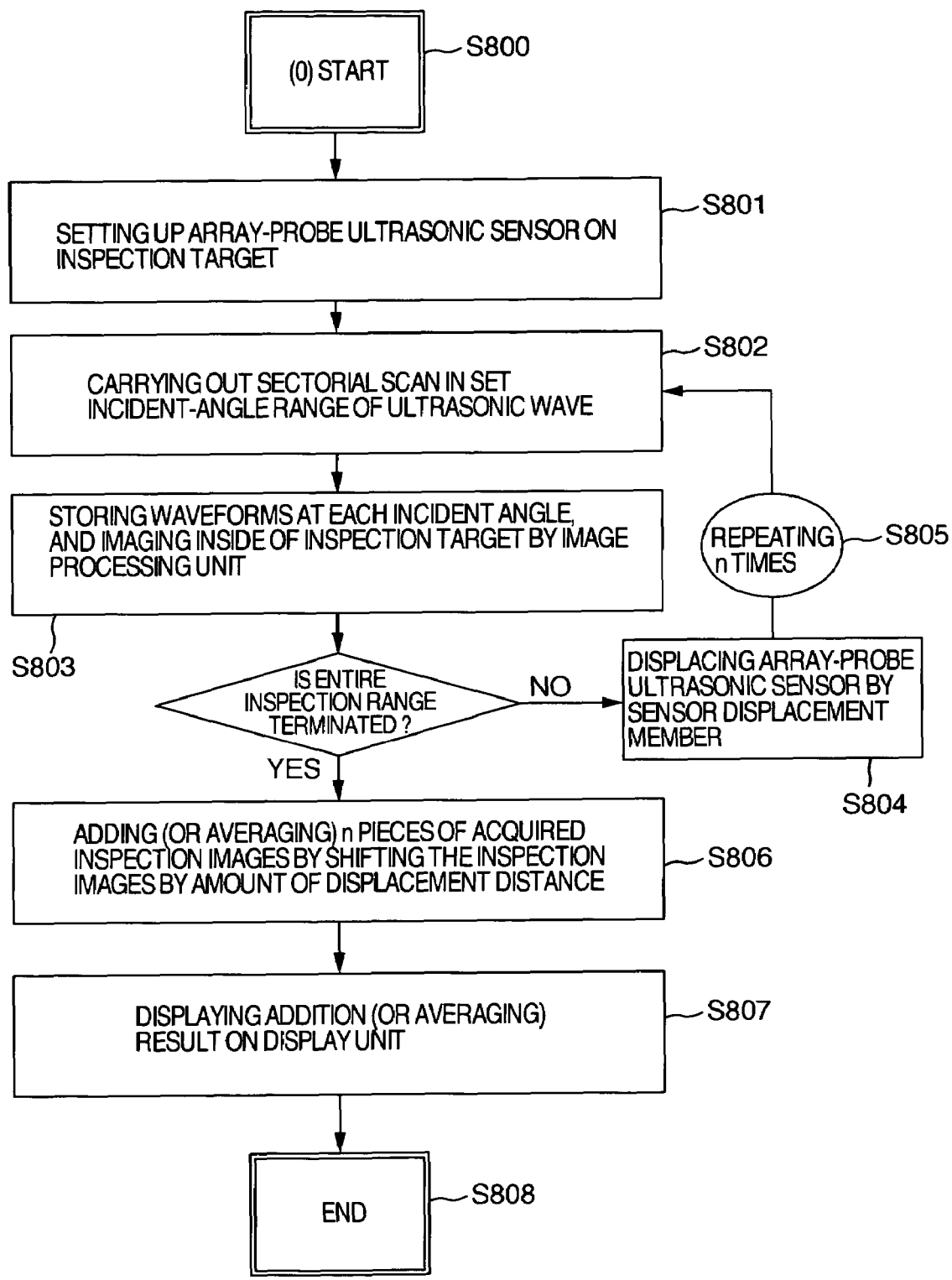
FIG. 8 is a flowchart for explaining a first example of processing steps according to the first embodiment of the present invention.

Next, referring to FIG. 8, the explanation will be given below concerning the processing steps in the first and second embodiments explained so far. Incidentally, this processing illustrated in FIG. 8 is executed by a predetermined program installed in the computer 102A.

On account of this, at first, the computer 102A starts the inspection after setting the inspection range, the focal depth of the array-probe ultrasonic sensor 101, and the incident-angle range of the ultrasonic wave at the transmission/reception unit 102 (S800). Next, the array-probe ultrasonic sensor 101 is set up on the inspection target (S801). After that, the sectorial scan is performed by changing the incident angle of the ultrasonic wave (S802). Next, the waveforms at the respective incident angles of the respective ultrasonic waves are stored and visualized by the transmission/reception unit 102 (S803). Moreover, here, it is checked whether or not the inspection in the entire inspection range has been terminated.

First, if the inspection in the entire inspection range has been not terminated, the array-probe ultrasonic sensor 101 is displaced to the next position by the sensor displacement member 107 (S804), then repeating the processings at S802 and S803 n times, i.e., until the inspection at all the positions has been terminated (S805). When, in this way, the inspection in the entire inspection range, i.e., the inspection from the inspection start position 101A to the inspection termination position 10C, has been terminated, the respective inspection images stored are added or averaged by shifting the inspection images by the amount equivalent to the displacement quantity of the array-probe ultrasonic sensor 101 (S806). Next, an inspection result acquired by the addition or averaging is displayed by the display unit 103 (S807), then terminating the processing (S808).

Here, in the case of the second embodiment explained in FIG. 6, i.e., the case of configuring the individual inspection images by taking the displacement quantity of the array-probe ultrasonic sensor 101 into consideration, in the processing at S806, the inspection images are added or averaged just as they are without shifting the inspection images. Incidentally, this processing is also executed by the computer 102A.

As a consequence, the processed image 502 illustrated in FIG. 5 and the processed image 602 illustrated in FIG. 6 turn out to be displayed on the display unit 103. Consequently, the above-described processing is the first processing steps according to the first embodiment of the present invention.

By the way, as the processing steps according to the embodiments of the present invention, there exist the following processing steps: Namely, every time the inspection images processed are acquired and stored, the inspection images are added or averaged one after another to be displayed. Accordingly, next, referring to FIG. 9, the explanation will be given below regarding the processing in this case.

Figure 9:
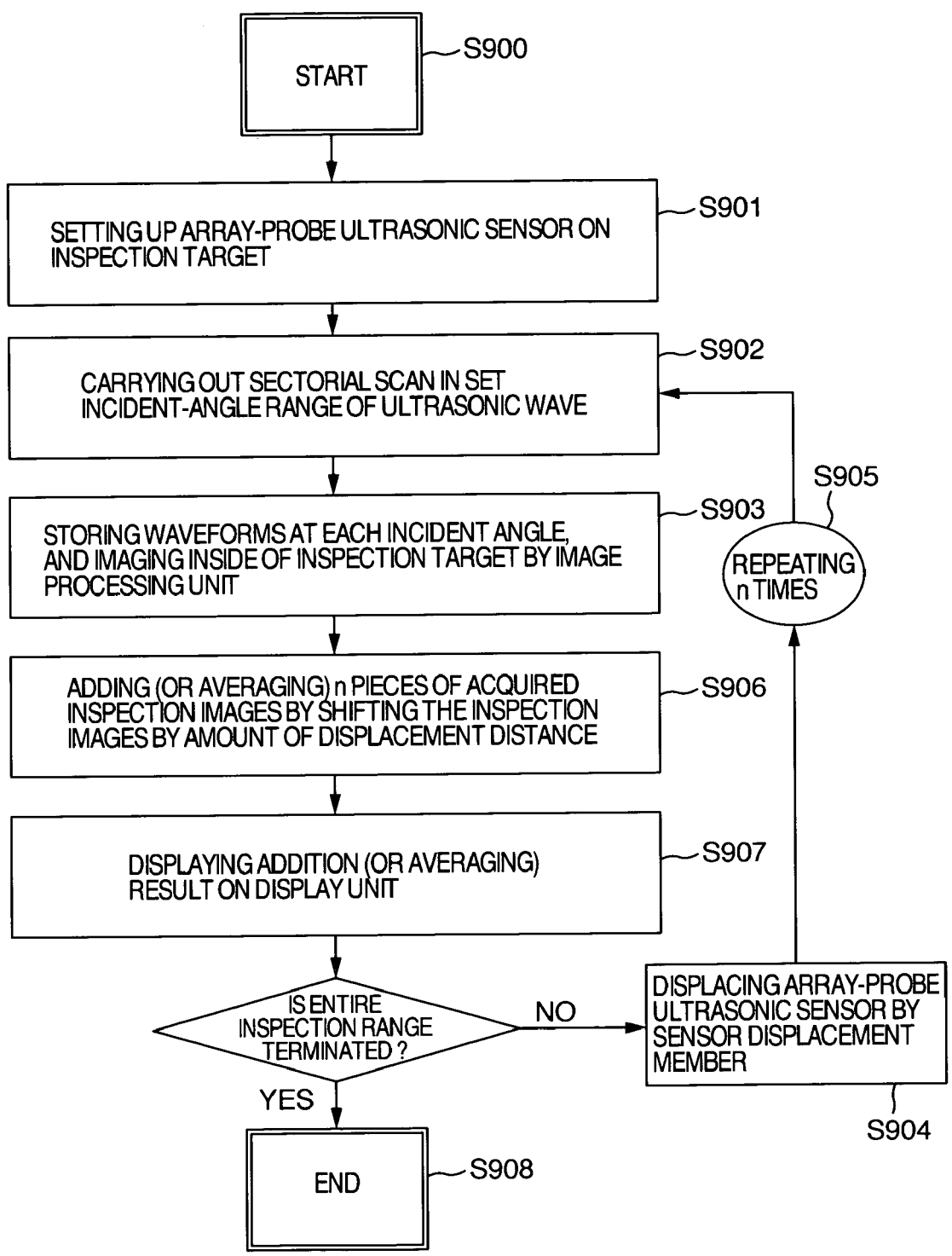
FIG. 9 is a flowchart for explaining a second example of the processing steps according to the first embodiment of the present invention.

This processing illustrated in FIG. 9 is also executed by the computer 102A. In this case as well, at first, the computer 102A starts the inspection after setting the inspection range, the focal depth of the array-probe ultrasonic sensor 101, and the incident-angle range of the ultrasonic wave at the transmission/reception unit (S900). Moreover, the array-probe ultrasonic sensor 101 is set up on the inspection target (S901). After that, the sectorial scan is performed by changing the incident angle of the ultrasonic wave (S902). Next, the waveforms at the respective incident angles of the respective ultrasonic waves are stored and visualized by the transmission/reception unit 102 (S903).

Next, the respective inspection images stored are added or averaged by shifting the inspection images by the amount equivalent to the displacement quantity of the array-probe ultrasonic sensor 101 (S906). Next, an inspection result acquired by the addition or averaging is displayed by the display unit 103 (S907).

Here, it is checked whether or not the inspection in the entire inspection range has been terminated. If the inspection in the entire inspection range has been not terminated, the array-probe ultrasonic sensor 101 is displaced to the next position by the sensor displacement member 107 (S904), then repeating the processings from S902 to S907 n times, i.e., until the inspection at all the positions has been terminated (S905). Furthermore, when the inspection in the entire inspection range, i.e., the inspection from the inspection start position 101A to the inspection termination position 10C, has been terminated, the processing is terminated after that (S908).

Accordingly, at this time as well, the processed image 502 illustrated in FIG. 5 and the processed image 602 illustrated in FIG. 6 turn out to be displayed on the display unit 103. Consequently, this processing is the second processing steps according to the first embodiment of the present invention. When comparing the second processing steps with the first processing steps illustrated in FIG. 8, the second processing steps add or average the inspection images one after another, thereby displaying the inspection images as the processed image sequentially. This allows the inspector to monitor the processed image (i.e., the processed image 502 or processed image 602) at any time. Accordingly, the characteristic of the second processing steps is the point which permits the inspector to perform the inspection while confirming the task situation.

Figure 10:
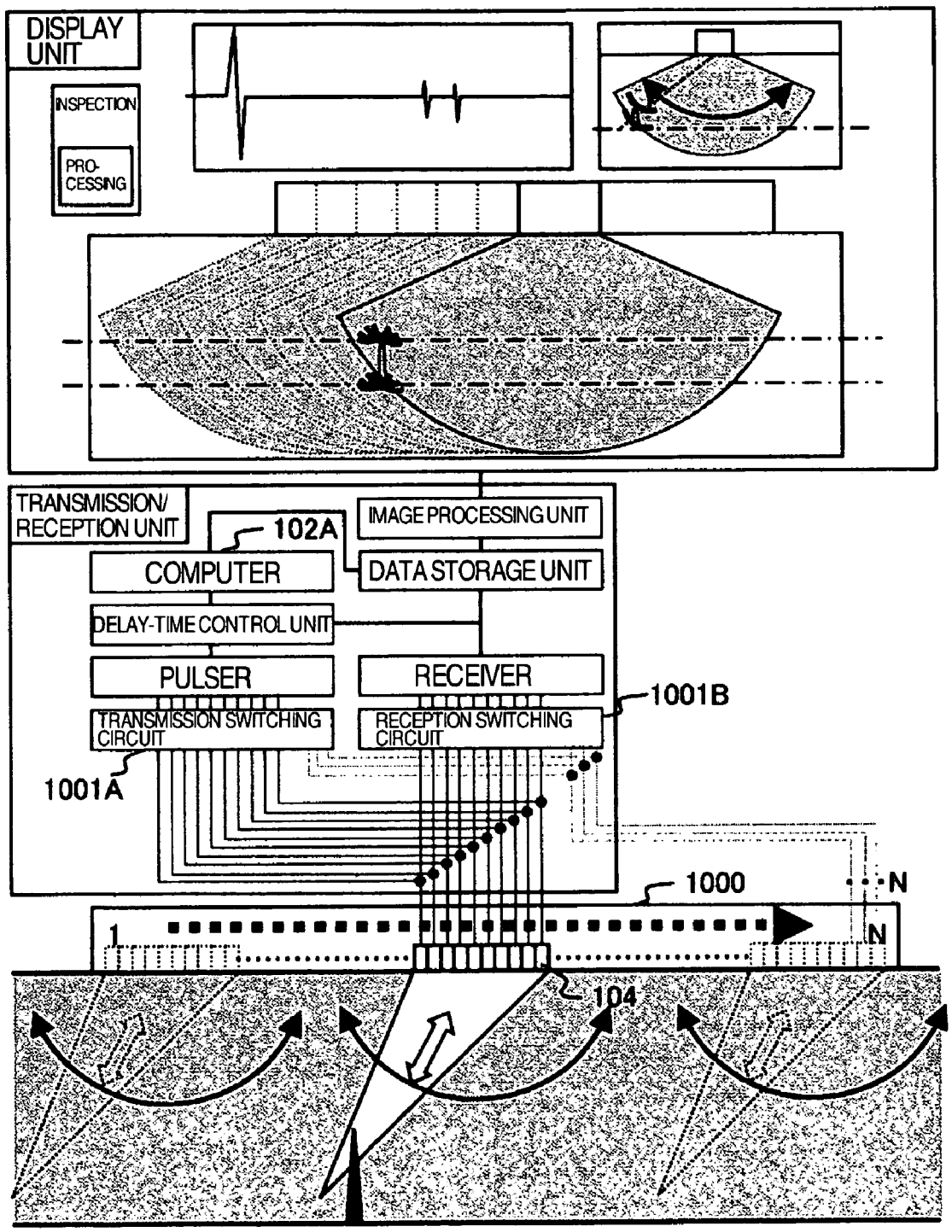
FIG. 10 is a configuration diagram for illustrating a second embodiment of the ultrasonic inspection method and the ultrasonic inspection equipment according to the present invention.

Next, referring to FIG. 10, the explanation will be given below concerning a third embodiment of the present invention. Here, the characteristic of this third embodiment is the following point: Namely, as an array-probe ultrasonic sensor 1000, an array-probe ultrasonic sensor is used which includes a plurality of piezoelectric vibration elements whose number is larger than the number of a plurality of piezoelectric vibration elements 104 needed for the operation as the original array-probe ultrasonic sensor. Moreover, in correspondence therewith, a transmission switching circuit 1001A and a reception switching circuit 1001B are provided in the transmission/reception unit 102. Incidentally, the illustration is omitted regarding part of connection lines ranging from each of the piezoelectric vibration elements 104 to the transmission switching circuit 1001A and the reception switching circuit 1001B.

Furthermore, in this third embodiment, taking advantage of the array-probe ultrasonic sensor 1000 of this kind allows implementation of the following operation: Namely, the displacement (i.e. scan) of the transmission position and reception position of the ultrasonic wave by the array-probe ultrasonic sensor, which is needed from the inspection start to the inspection termination, can be acquired by electrically switching the piezoelectric vibration elements 104 inside the array-probe ultrasonic sensor 1000. Accordingly, here, the sensor displacement member 107 in the embodiment in FIG. 1 is unnecessary. In accompaniment therewith, the scan-member control unit 105 and the displacement-quantity detection unit 106 are also unnecessary. The other configurations, however, are the same as those in the embodiment in FIG. 1.

The ultrasonic-wave scan method based on the electrical switching for the piezoelectric vibration elements 104 is referred to as "electronic scan scheme". Accordingly, this embodiment in FIG. 10 allows the transmission position and reception position of the ultrasonic wave to be scanned inside the array-probe ultrasonic sensor 1000. This makes unnecessary the mechanical sensor displacement member which was needed in the first and second embodiments. Consequently, it becomes possible to inspect the inside of the inspection target 100 with the array-probe ultrasonic sensor 1000 fixed. As a result, it becomes possible to implement the higher-speed scan.

Next, the explanation will be given below regarding the operation of this third embodiment. At first, the array-probe ultrasonic sensor 1000 is set up in the inspection range on the inspection target 100. At this time, the set-up is performed such that the element situated at the farthest end of the piezoelectric vibration elements 104 falls at the inspection start position of the inspection range. Moreover, the transmission of the ultrasonic wave 108 and reception of echoes are carried out, using the elements whose number is to be used at a one-time inspection from the farthest-end element, such as 16 elements or 32 elements, i.e., an arbitrary number of elements needed for the operation as the original array-probe ultrasonic sensor.

Now, assume that the number of the elements at this time is equal to, e.g., 16. Here, next, at least one or more elements of the piezoelectric vibration elements 104 are shifted inside the array-probe ultrasonic sensor 1000. Then, using the 16 pieces of piezoelectric vibration elements 104 to be used at the one-time inspection, the ultrasonic wave 108 is generated as described earlier. In addition, the operation is performed which ranges from the carrying-out of the transmission and reception of the ultrasonic wave to the creation of the inspection images by the computer 102A. This operation is repeated n times until the inspection termination position, thereby acquiring n pieces of inspection images.

Subsequently, these n pieces of inspection images are added or averaged at the respective inspection positions by shifting the inspection images by the amount equivalent to the shifted elements. Here, the element number to be displaced for each one-time inspection can be arbitrarily determined. For example, if the more detailed inspection images are wished to be acquired, the inspection images are acquired as many as possible by performing the shifting on one element basis. If the details to some extent are preferable enough, the inspection is carried out by performing the shifting on two-or-more elements basis.

These n pieces of inspection images acquired in this way are added or averaged on each inspection basis by shifting the inspection images by the pixel number of the inspection images equivalent to the displacement quantity of the elements. Furthermore, the element displacement quantity at this time is calculated assuming that element spacing between the piezoelectric vibration elements of the array-probe ultrasonic sensor 1000 has been already known. Here, the addition or averaging method for the inspection images in this third embodiment is basically the same as the method explained earlier in the first and second embodiments. Consequently, the explanation thereof here will be omitted.

Figure 11:
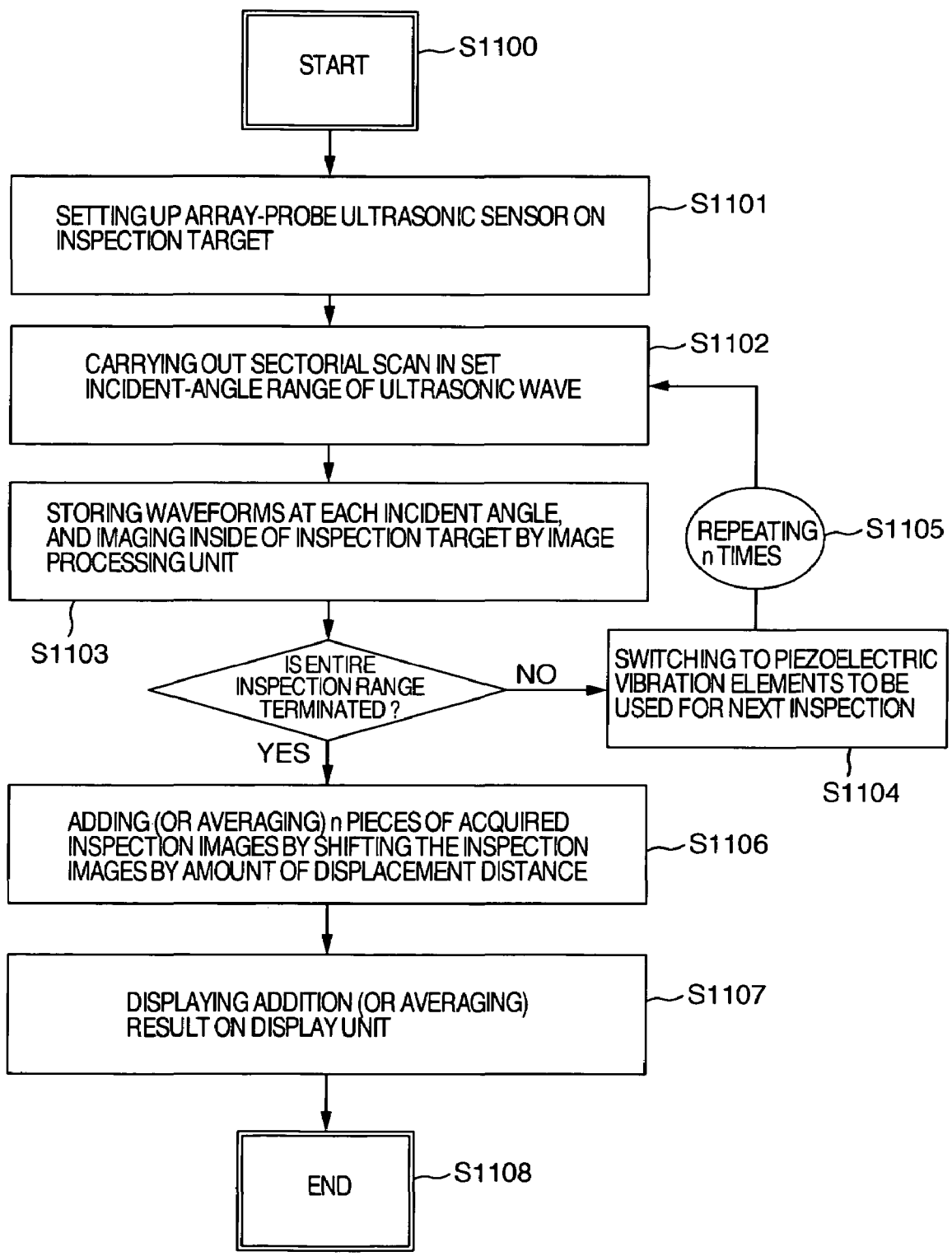
FIG. 11 is a flowchart for explaining a first example of processing steps according to the second embodiment of the present invention.

Next, referring to FIG. 11, the explanation will be given below concerning the carrying-out steps in this third embodiment. At first, the inspection is started after setting the inspection range, the focal depth of the array-probe ultrasonic sensor 1000, the number of the piezoelectric vibration elements 104 to be used at a one-time inspection, and the incident-angle range of the ultrasonic wave at the transmission/reception unit 102 (S1100). Next, the array-probe ultrasonic sensor 1000 is set up on the inspection target 100 (S1101). After that, the sectorial scan is performed by changing the incident angle of the ultrasonic wave (S1102). Next, the waveforms at the respective incident angles of the respective ultrasonic waves are stored and imaged by the computer 102A (S1103).

Moreover, first, if the inspection in the entire inspection range has been not terminated, a plurality of (e.g., 16 pieces of) piezoelectric vibration elements 104, which are being used for the inspection inside the array-probe ultrasonic sensor 1000, are switched to piezoelectric vibration elements to be used for the next inspection, thereby displacing the transmission position and reception position of the ultrasonic wave (S1104). Here, this switching is performed by the transmission switching circuit 1001A and the reception switching circuit 101B. Then, the sectorial scan and the imaging are repeated n times until the entire inspection has been terminated (S1105).

Furthermore, when the inspection in the entire inspection range has been terminated, the respective inspection images stored by the computer 102A are added or averaged by shifting the inspection images by the amount equivalent to the displacement quantity of the piezoelectric vibration elements 104 inside the array-probe ultrasonic sensor 1000 (S1106). In this case as well, however, as explained in FIG. 6, in the case configuring the individual inspection images by taking the displacement quantity of the array-probe ultrasonic sensor 1000 into consideration, the inspection images are added or averaged without shifting the inspection images. In addition, an inspection result acquired hereby is displayed on the display unit 103 (S1107), then terminating the inspection (S1108).

Figure 12:
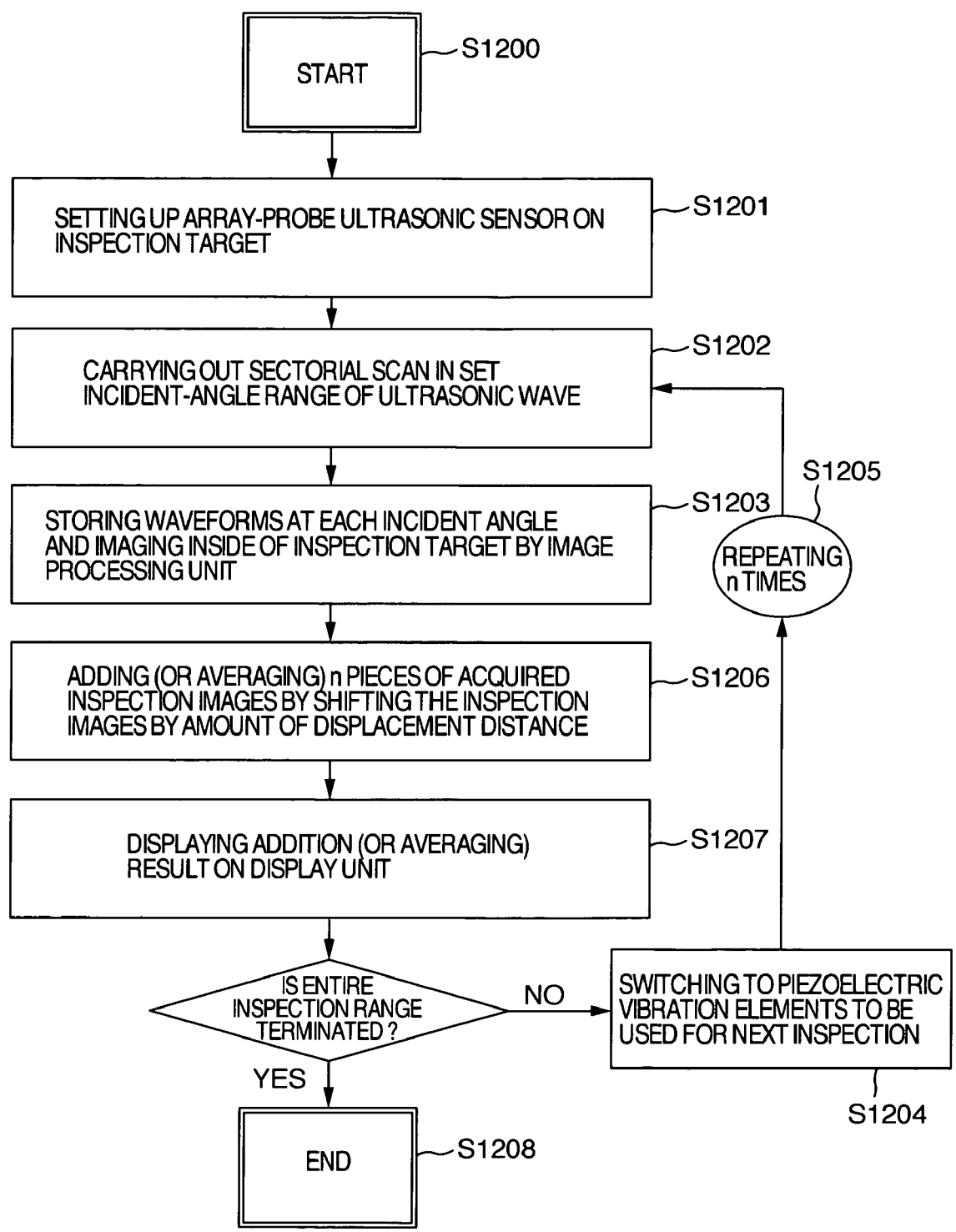
FIG. 12 is a flowchart for explaining a second example of the processing steps according to the second embodiment of the present invention.

Also, as the processing steps according to this embodiment, there exist the following processing steps: Namely, every time the inspection images are stored, the inspection images are added or averaged one after another to be displayed. Next, referring to FIG. 12, the explanation will be given regarding this processing. At first, the inspection is started after setting the inspection range, the focal depth of the array-probe ultrasonic sensor 1000, and the incident-angle range of the ultrasonic wave (S1200). Next, the array-probe ultrasonic sensor 1000 is set up on the inspection target (S1201). After that, the sectorial scan is performed by changing the incident angle of the ultrasonic wave (S1202). Next, the waveforms at the respective incident angles of the respective ultrasonic waves are stored and imaged by the computer 102A (S1203).

If there exist two or more pieces of inspection images, these inspection images are added or averaged by the computer 102A by shifting the inspection images by the amount equivalent to the displacement quantity of the piezoelectric vibration elements 104 inside the array-probe ultrasonic sensor 1000 (S1206). Then, a result acquired hereby is displayed on the display unit 103 (S1207).

Meanwhile, if the inspection in the entire inspection range of the inspection images has been not terminated, the piezoelectric vibration elements 104, which are being used for the inspection inside the array-probe ultrasonic sensor 1000, are switched to the piezoelectric vibration elements 104 to be used for the next inspection, thereby displacing the transmission/reception position of the ultrasonic wave (S1204). Here, this switching is performed by the transmission switching circuit 1001A and the reception switching circuit 1001B. Then, the sectorial scan and the imaging are repeated n times until the entire inspection has been terminated (S1205). Furthermore, if the inspection in the entire inspection range has been terminated, the inspection is terminated (S1208).

By the way, in the first to third embodiments explained so far, the explanation has been given concerning the embodiment where the present application is applied to the flat-plane-shaped inspection target thereby to displace the array-probe ultrasonic sensor linearly, and the embodiment where the piezoelectric vibration elements inside the array-probe ultrasonic sensor are switched thereby to displace the transmission/reception position of the ultrasonic wave and to carry out the inspection. Next, referring to FIG. 13, the explanation will be given below concerning a fourth embodiment of the present invention. This embodiment is a one which is preferable for the case where the inspection target is of a curve-surface or complicated configuration like the portion of a pipe along its circumferential direction.

Here, in the case like this, there exist the following two cases: Namely, the case where, like the embodiment in FIG. 1, the array-probe ultrasonic sensor is mechanically scanned in compliance with the surface configuration of the inspection target thereby to acquire the inspection images, and the case where, like the embodiment in FIG. 10, the surface configuration itself of the array-probe ultrasonic sensor has become basically the same configuration as the one of the inspection target. Here, the former case will be explained in detail. Accordingly, in this embodiment as well, the equipment configuration is the same as the one in FIG. 1. What differs therefrom is only the point that, as illustrated in FIG. 13, the displacement direction of the array-probe ultrasonic sensor 101 by the sensor displacement member 107 becomes the curve-line direction along the surface of the curve-surface-shaped inspection target 1300.

Figure 13:
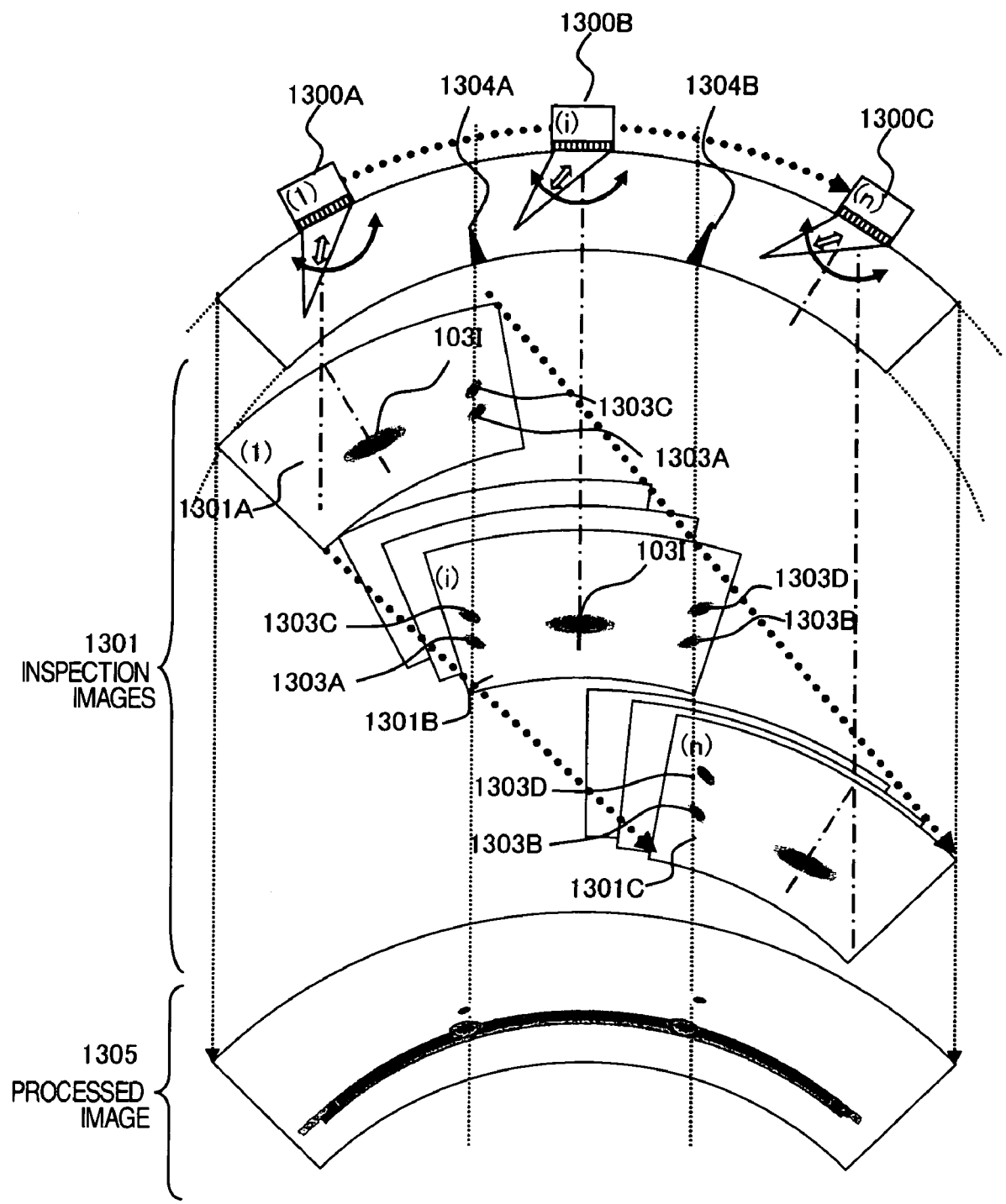
FIG. 13 is an explanatory diagram for illustrating an example of the addition or averaging processing of inspection images according to a third embodiment of the present invention.

In FIG. 13, the curve-surface-shaped inspection target 1300 is illustrated by the cross section resulting from seeing a tube member, e.g., pipe, from the longitudinal direction. In this cross section, a 1st inspection image (1) 1301A is an inspection image measured at an inspection start position (1) 1302A. An i-th inspection image (i) 1301B and an n-th inspection image (n) 1301C correspond to an inspection position (i) 1302B and an inspection position (n) 1302C, respectively. Consequently, n pieces of inspection images 1301 are shown which are acquired as a result of the inspection where the sectorial scan is performed at each position.

In this embodiment, the curve-surface-shaped inspection target like a pipe is assumed as the inspection target. Accordingly, the surface on which the array-probe ultrasonic sensor 101 is set up and the bottom surface are substantially parallel to each other. As a result, the bottom echo 103I is acquired directly below the set-up position of the array-probe ultrasonic sensor 101. At this time, if the defect enters from the bottom side, defect corner echoes 1303A and 1303B and defect tip echoes 1303C and 1303D are observed respectively in correspondence with the positions at which there exist the respective defects 1304A and 1304B.

Then, the addition or averaging processing is applied to these inspection images by shifting the inspection images by the pixel number equivalent to the displacement quantity of the array-probe ultrasonic sensor 101, e.g., the displacement quantity thereof from the position 1300A to the position 1300B. Here, what differs from the first and second embodiments is the point that the inspection target 1300 is of the curve-surface configuration, and that, as a result, influences of this configuration need to be corrected when processing the inspection images. For this purpose, in this embodiment, the surface-configuration data on the inspection target 1300 measured in advance is supplied to the computer 102A. Otherwise, angle measurement function for the array-probe ultrasonic sensor 101 is provided to the displacement-quantity detection unit 106. These measures allow implementation of the rotation correction for the inspection images at the time of the addition or averaging of the images.

Concretely, the computer 102A performs the addition or averaging processing by shifting the inspection images from the inspection start position by amount of the displacement quantity of central position of the array-probe ultrasonic sensor 101, and by rotating the inspection images by amount of the rotation angle from the inspection start position. This processing allows acquisition of a rotation-corrected processed image 1305.

In the processed image 1305, in each of the defect corner echoes 1303A and 1303B and the defect tip echoes 1303C and 1303D, only the signal at a real defect position is caused to selectively remain by the superimposition of the ultrasonic waves entering from the various angles. This signal is used for confirming the defect position and evaluating the defect depth. Moreover, even when the surface configuration is complicated, performing the processing similar to the above-described one makes it possible to process the inspection images.

Figure 14:
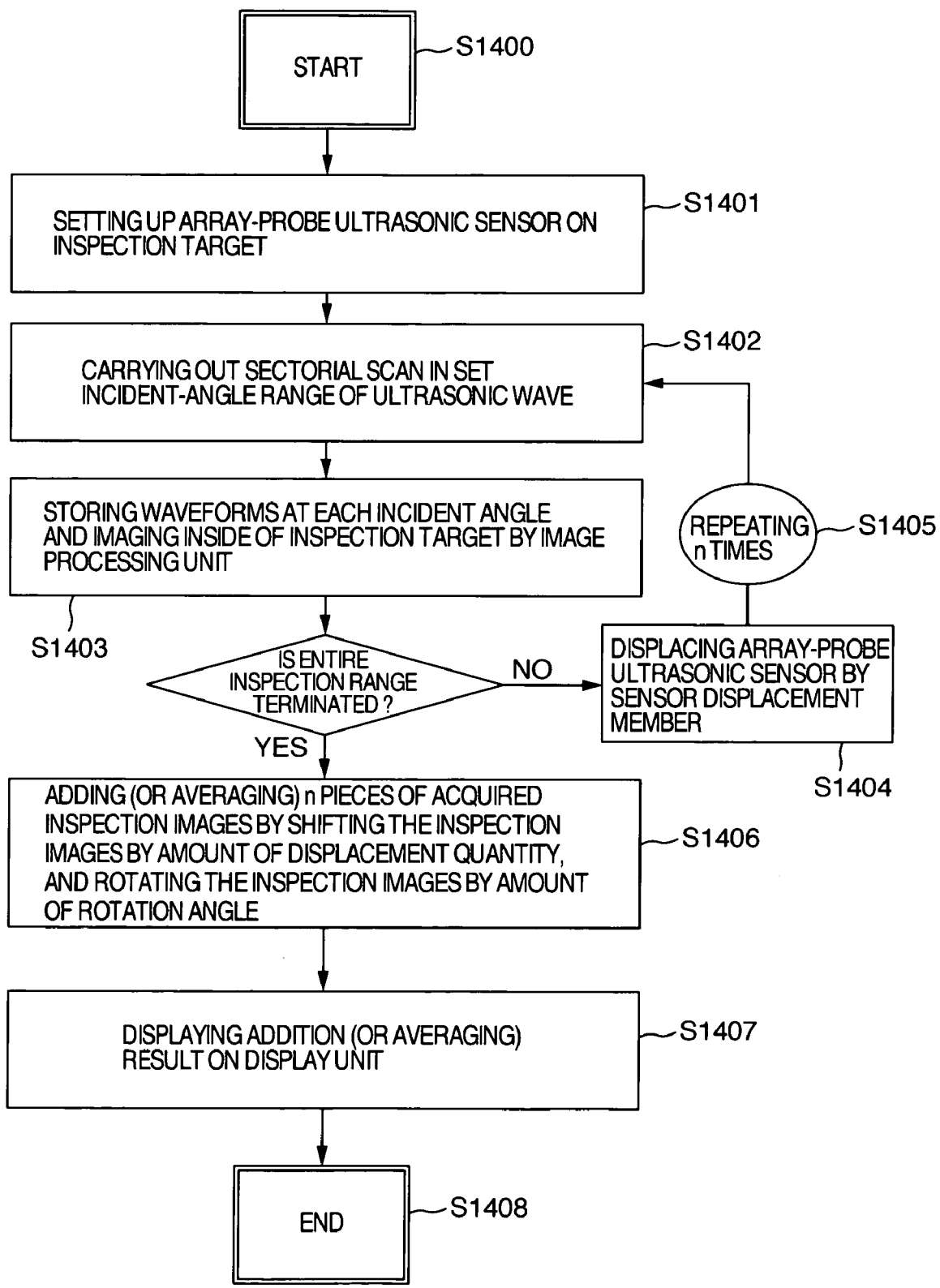
FIG. 14 is a flowchart for explaining an example of processing steps according to the third embodiment of the present invention.

Next, referring to FIG. 14, the explanation will be given below concerning the processing steps according to the fourth embodiment. At first, the inspection is started after setting the inspection range, the focal depth of the array-probe ultrasonic sensor 101, and the incident-angle range of the ultrasonic wave (S1400). Next, the array-probe ultrasonic sensor 101 is set up on the inspection target (S1401). After that, the sectorial scan is performed by changing the incident angle of the ultrasonic wave (S1402). Next, the waveforms at the respective incident angles of the respective ultrasonic waves are stored, then being visualized by the computer 102 (S1403).

Moreover, at first, if the inspection in the entire inspection range has been not terminated, the array-probe ultrasonic sensor 101 is displaced along the surface of the inspection target 1300 by the sensor displacement member 107 (S1404). Then, the sectorial scan and the imaging are repeated n times until the entire inspection has been terminated (S1405). Meanwhile, if the inspection in the entire inspection range has been terminated, the respective inspection images stored in the computer 102 are added or averaged by shifting the inspection images from the inspection start position 1300A by amount of the displacement quantity of central position of the array-probe ultrasonic sensor 101, and by rotating the inspection images by amount of the rotation angle from the inspection start position (S1406). Next, an inspection result acquired by the addition or averaging is displayed by the display unit 103 (S1407), then terminating the processing (S1408).

As having been explained so far, according to the above-described embodiments, the inspection (i.e., sectorial-scan inspection) of the inside of an inspection target is performed by changing the incident angle of the ultrasonic wave oscillated from the array-probe ultrasonic sensor 101. Also, the set-up position of the array-probe ultrasonic sensor or the transmission/reception position of the ultrasonic wave is sequentially displaced. Moreover, the inspection images acquired at the respective inspection positions are visualized by adding or averaging the inspection images while shifting the images by the amount of the displacement quantity of the array-probe ultrasonic sensor 101 or the transmission/reception position of the ultrasonic wave. This allows the inspection image to be configured by the superimposition of the ultrasonic waves entering from the various angles.

Accordingly, according to the above-described embodiments, it becomes possible to acquire the convergence effect on the ultrasonic wave without setting the focal depth in particular detail. Also, as a result, it becomes possible to acquire the high-resolution inspection images at almost all the depth positions. This permits implementation of the high-accuracy nondestructive inspection.

Also, according to the above-described embodiments, it becomes possible to carry out the sectorial scan in such a manner that the ultrasonic wave has been beforehand converged from the array-probe ultrasonic sensor 101. This allows the diffusion and attenuation of the ultrasonic wave to be suppressed even if the inspection target is thick and the propagation distance of the ultrasonic wave is long. Consequently, it becomes possible to clear the diffusion and attenuation of the ultrasonic wave which has been the problem in the synthetic aperture method, thereby allowing an enhancement in the S/N ratio of the inspection image. Furthermore, the addition or averaging of the inspection images makes it possible to reduce the random noises such as electric noise, thereby allowing the enhancement in the S/N ratio of the inspection image.

Moreover, according to the above-described embodiments, by selecting and setting the simple methodology such as the addition or averaging with respect to the time needed for processing the inspection images, it becomes possible to reduce the processing throughput on the computer 102A. Consequently, it turns out that not so much time is required for the processing. This characteristic allows a defect to be speedily evaluated even on an actual site of the inspection in such a manner that the high-resolution and high-S/N-ratio inspection image has been acquired beforehand.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An ultrasonic inspection method, comprising the steps of:
displacing transmission/reception position of ultrasonic wave relative to an inspection target by an array-probe ultrasonic sensor,
performing inspection of said inspection target in accordance with sectorial scan scheme by using said array-probe ultrasonic sensor at said plurality of transmission/reception positions,
creating a single image from respective inspection result images at said plurality of transmission/reception positions,
grasping quantity of said displacement of said transmission/reception position of said ultrasonic wave, and
creating said single image by applying an addition or averaging processing to said respective inspection result images by shifting said images by the amount equivalent to said quantity of said displacement.

2. Ultrasonic inspection equipment, comprising:
an array-probe ultrasonic sensor,
scan means for displacing transmission/reception position of ultrasonic wave by said array-probe ultrasonic sensor,
transmission/reception means for transmitting/receiving a driving signal and a reception signal between said transmission/reception means and said array-probe ultrasonic sensor, and allocating a delay time to said driving signal thereby to change convergence position and incident angle of said ultrasonic wave,
a computer for applying an addition or averaging processing to ultrasonic-wave transmission/reception results at said plurality of ultrasonic-wave transmission/reception positions by shifting said ultrasonic-wave transmission/reception results by the amount equivalent to quantity of said displacement, and
display means for displaying a processing result in said computer as a single inspection image.

3. An ultrasonic inspection method, comprising the steps of:
changing incident angle of ultrasonic wave relative to an inspection target by using an array-probe ultrasonic sensor,
displacing set-up position of said array-probe ultrasonic sensor in said inspection target, thereby to sequentially acquire inspection images on each set-up position basis, and visualizing said inspection images by adding or averaging said inspection images while sequentially shifting said inspection images by the amount equivalent to quantity of said displacement of said array-probe ultrasonic sensor.

4. The ultrasonic inspection method according to claim 3, wherein, in said addition or averaging of said inspection images, inclination angle of each inspection image will be corrected in response to inclination of surface of said inspection target, said inclination appearing in said displacement of said set-up position of said array-probe ultrasonic sensor in said inspection target.

5. An ultrasonic inspection method, comprising the steps of:
  changing incident angle of ultrasonic wave relative to an inspection target by using part of piezoelectric vibration elements inside an array-probe ultrasonic sensor,
  displacing ultrasonic-wave transmission/reception position of said array-probe ultrasonic sensor in said inspection target by sequentially switching said part of said piezoelectric vibration elements inside said array-probe ultrasonic sensor, thereby to sequentially acquire inspection images on each ultrasonic-wave transmission/reception position basis, and
  visualizing said inspection images on each ultrasonic-wave transmission/reception position basis by adding or averaging said inspection images while sequentially shifting said images by the amount equivalent to quantity of said displacement of said part of said piezoelectric vibration elements inside said array-probe ultrasonic sensor.

6. Ultrasonic inspection equipment, comprising:
  an array-probe ultrasonic sensor including a plurality of piezoelectric vibration elements,
  a pulser for supplying a transmission signal to each piezoelectric vibration element of said array-probe ultrasonic sensor,
  a receiver for inputting a reception signal from each piezoelectric vibration element of said array-probe ultrasonic sensor,
  a delay control unit for setting a delay time to said transmission signal and said reception signal, said delay time being different on each piezoelectric-vibration-element basis,
  a data storage unit for storing ultrasonic waveforms received at said array-probe ultrasonic sensor,
  sensor displacement means for scanning said array-probe ultrasonic sensor with respect to an inspection target,
  a scan control unit for controlling said scan,
  a displacement-quantity detection unit for measuring displacement quantity of said array-probe ultrasonic sensor,
  an image-processing computer for generating a plurality of inspection images from said ultrasonic waveforms stored in said data storage unit, and adding or averaging said plurality of inspection images by shifting said images by the amount of said displacement quantity measured in said displacement-quantity detection unit of said array-probe ultrasonic sensor, and
  a display unit for displaying said inspection images and an inspection image acquired from said addition.

7. The ultrasonic inspection equipment according to claim 6, wherein said computer is a computer which, in adding or averaging said plurality of inspection images, will correct inclination angle of each inspection image in response to inclination of surface of said inspection target, said inclination appearing in said displacement of said set-up position of said array-probe ultrasonic sensor in said inspection target.

8. The ultrasonic inspection equipment according to claim 6, further comprising:
  processing-contents switch means for switching between normal inspection operations and said inspection operation based on said addition processing or said averaging processing.

9. Ultrasonic inspection equipment, comprising:
  an array-probe ultrasonic sensor including a plurality of piezoelectric vibration elements whose number is larger than a number needed for operation as said array-probe ultrasonic sensor,
  a pulser for supplying a transmission signal to each piezoelectric vibration element of said array-probe ultrasonic sensor,
  a transmission switching circuit for switching a piezoelectric vibration element to which, of said respective piezoelectric vibration elements of said array-probe ultrasonic sensor, said output from said pulser will be supplied,
  a receiver for inputting a reception signal from each piezoelectric vibration element of said array-probe ultrasonic sensor,
  a reception switching circuit for switching a piezoelectric vibration element which, of said respective piezoelectric vibration elements of said array-probe ultrasonic sensor, will supply said reception signal to said receiver,
  a delay control unit for setting a delay time to said transmission signal and said reception signal, said delay time being different on each piezoelectric-vibration-element basis,
  a data storage unit for storing ultrasonic waveforms received at said array-probe ultrasonic sensor,
  sensor displacement means for scanning said array-probe ultrasonic sensor with respect to an inspection target,
  a scan control unit for controlling said scan,
  a displacement-quantity detection unit for measuring displacement quantity of said array-probe ultrasonic sensor,
  an image-processing computer for generating a plurality of inspection images from said ultrasonic waveforms stored in said data storage unit, and adding or averaging said plurality of inspection images by shifting said images by the amount of said displacement quantity measured in said displacement-quantity detection unit of said array-probe ultrasonic sensor, and
  a display unit for displaying said inspection images and an inspection image acquired from said addition.

10. The ultrasonic inspection equipment according to claim 9, further comprising:
  processing-contents switch means for switching between normal inspection operations and said inspection operation based on said addition processing or said averaging processing.

* * * * *